United States Patent [19]
Kappes et al.

[11] Patent Number: 6,001,985
[45] Date of Patent: *Dec. 14, 1999

[54] FUSION PROTEIN DELIVERY SYSTEMS AND USES THEREOF

[75] Inventors: John Christopher Kappes; Xiaoyun Wu, both of Birmingham, Ala.

[73] Assignee: University of Alabama Research Foundation, Birmingham, Ala.

[ * ] Notice: This patent is subject to a terminal disclaimer.

[21] Appl. No.: 08/947,516

[22] Filed: Sep. 29, 1997

Related U.S. Application Data

[63] Continuation of application No. 08/421,982, Apr. 14, 1995, abandoned.

[51] Int. Cl.$^6$ .................................................. C07H 21/04
[52] U.S. Cl. ...................... 536/23.4; 435/320.1; 435/367
[58] Field of Search .............................. 435/69.1, 320.1, 435/367; 530/350, 300; 536/23.1, 23.4

[56] References Cited

U.S. PATENT DOCUMENTS

| | | | |
|---|---|---|---|
| 5,175,099 | 12/1992 | Wills ...................................... | 435/69.7 |
| 5,378,806 | 1/1995 | Willis ...................................... | 530/350 |
| 5,861,161 | 1/1999 | Cohen et al. ......................... | 424/192.1 |

FOREIGN PATENT DOCUMENTS

| | | |
|---|---|---|
| 356021 | 2/1990 | European Pat. Off. . |
| 275259 | 1/1990 | Germany . |
| WO 9015875 | 12/1990 | WIPO . |
| WO 9200987 | 1/1992 | WIPO . |
| WO 93/25235 | 12/1993 | WIPO . |
| WO 9324632 | 12/1993 | WIPO . |
| WO 9417825 | 8/1994 | WIPO . |
| WO 9516705 | 6/1995 | WIPO . |
| WO 9526361 | 10/1995 | WIPO . |
| WO 9607741 | 3/1996 | WIPO . |
| WO 9611696 | 4/1996 | WIPO . |
| WO 9736481 | 10/1997 | WIPO . |

OTHER PUBLICATIONS

Wu et al. The First National Conference on Human Retroviruses and Related Infections. Washington, DC., 1993.

Percy et al., "A poliovirus replicon containing the chloramphenicol acetyltransferase gene can be used to study the replication and encapsidation of poliovirus RNA", J. Virol. 66(8):5040–5046, Aug. 1992.

Hu et al., "Analysis and function of viral protein X (VPX) of HIV–2", Virol. 173: 624–630, 1989.

Zhao et al., "Biochem. Mechanism of HIV–1 Vpr function", J. Biol. Chem. 269: 15577–15582, Jun. 1994.

Natsoulis et al., Targeting of a nuclease to murine leukemia virus capsids inhibit viral multiplication, Proc. Natl. Acad. Sci. USA 92:364–368, Jan. 1995.

Natsoulis and Boeke, "New antiviral strategy using capsid-–nuclease fusion proteins", Nature 352: 632–635, Aug. 1991.

Wu et al., "Targeting foreign proteins to human immunodeficiency viruses types 1 and 2 via fusion with Vpr and Vpx", Biol. Abstr./RRM 47(4): MT–323, Ref. No. 66007, Jan. 1995.

Wu et al., "Inhibition of HIV–1 replication by targeting Vpr fusion proteins to virions", Biol. Abstr./RRM 47(4): MT–323, Ref. No. 66020, Jan. 1995.

Kappes et al, "The HIV Vpx and Vpr genes mediate virion incorporation of nuclease fusion proteins", J. Biol. Chem. Suppl. 21(A): 162, Ref. No. J513, Jan. 1994.

Kappes et al., "Targeting foreign proteins to HIV particles via fusion with Vpr and Vpx", J. Biol. Chem. Suppl. 21(A): 395, Ref. No. C6–328, Mar. 1995.

Wu et al. "HIV/SIV Virion Associated Accessory Genes Mediate Efficient Packaging of Nuclease Fusion Proteins Into The Virus Particle," The First National Conference on Human Retroviruses and Related Infections, Washington DC (1993).

Kappes et al. "Intracellular Transport And Virion Incorporation of vpx Requires Interaction With Other Virus Type–Specific Components," J. Virol. 193: 222–223 (1993).

Wu et al. "Targeting Foreign Proteins To Human Immunodeficiency Virus Particles Via Fusion With Vpr and Vpx," (Revised Manuscript, #JVI 1529–94), J. Virology, vol. 69, pp. 3389–3398 (1995).

Orkin et al. "Report And Recommendations Of The Panel To Assess The NIH Investment In Research On Gene Therapy," *NIH Panel Report*, Dec. 1995. Entire Report.

Tristem et al. "Evolution Of the Primate Lentiviruses: Evidence From Vpx and Vpr," EMBO J 11:3405–3412 (1992).

Tristem et al. "Origin Of Vpx In Lentiviruses," Nature 347:341–342.39 (1990).

Wu et al. "Inhibition Of Human And Simian Immunodeficiency Virus Protease Function By Targeting Vpx–Protease– Mutant Fusion Protein Into Viral Particles," J. Virol. 3378–3384 (Jun. 1996).

Liu et al. "Incorporation Of Functional Human Immunodeficiency Virus Type 1 Integrase Into Virions Independent Of The Gag/Pol Precursor Protein," (Revised Manuscript, #JVI 548–97) J. Virology, vol. 71, pp. 7704–7710 (1997).

Wu et al. "Functional RT and IN Incorporated Into HIV–1 Particles Independent Of The Gag/Pol Precursor Protein," EMBO J 16: 0, 101–109 (1997).

(List continued on next page.)

*Primary Examiner*—Nancy Degen
*Assistant Examiner*—Irem Yucel
*Attorney, Agent, or Firm*—Gifford, Krass, Groh, Sprinkle, Anderson & Citkowski, P.C.

[57] ABSTRACT

The present invention provides a composition of matter, comprising: DNA encoding a viral Vpx protein fused to DNA encoding a virus inhibitory protein. In another embodiment of the present invention, there is provided a composition of matter, comprising: DNA encoding a viral Vpr protein fused to DNA encoding a virus inhibitory protein. Also provided are various methods of delivering a virus inhibitory molecule to a target in an animal. Further provided is a pharmaceutical composition.

24 Claims, 11 Drawing Sheets

OTHER PUBLICATIONS

Lee et al. "The role of vpx in the life cycle of HIV–2," submitted to the Proceedings of the Third Annual "Colloque Des Cent Gardes" (1988).

Kappes et al. "Human Immunodeficiency Virus Type 2 vpx Protein Augments Viral Infectivity," Virology, 184, 197–209 (1991).

Kappes et al. "Identification of a Novel Retroviral Gene Unique to Human Immunodeficiency Virus Type 2 and Simian Immunodeficiency Virus SIV$_{MAC}$," vol. 62, No. 9, pp. 3501–3505 (Sep. 1988).

Wu et al. "Localization of the Vpx Packaging Signal within the C Terminus of the Human Immunodeficiency Virus Type 2 Gag Precursor Protein," J. Virol., vol. 68, No. 10, pp. 6161–6169 (Oct. 1994).

Akari et al. "Biological characterization of human immunodeficiency virus type 1 and type 2 mutants in human peripheral blood mononuclear cells," Arch. Virol. (1992) 123: 157–167.

Balotta et al. "Antisense Phosphorothioate Oligodeoxynucleotides Targeted to the vpr Gene Inhibit Human Immunodeficiency Virus Type 1 Replication in Primary Human Macrophages," J. Virol., vol. 67, No. 7, pp. 4409–4414 (Jul. 1993).

Cohen et al. "Human Immunodeficiency Virus vpr Product Is a Virion–Associated Regulatory Protein," J. Virol., vol. 64, No. 6, pp. 3097–3099 (Jun. 1990).

Dedera et al. "Viral Protein R of Human Immunodeficiency Virus Types 1 and 2 Is Dispensable for Replication and Cytopathogenicity in Lymphoid Cells," J. Virol., vol. 63, No. 7, pp. 3205–3208 (Jul. 1989).

Desrosiers. "HIV with Multiple Gene Deletions as a Live Attenuated Vaccine for AIDS," AIDS Research and Human Retroviruses, vol. 8, No. 3, pp. 411–421 (Nov. 3, 1992).

Di Marzio et al. "Mutational Analysis of Cell Cycle Arrest, Nuclear Localization, and Virion Packaging of Human Immunodeficiency Virus Type 1 Vpr," J. Virol., vol. 69, No. 12, pp. 7909–7916 (Dec. 1995).

Gibbs et al. Construction and In Vitro Properties of SIV$_{mac}$ Mutants with Deletions in "Nonessential" Genes, AIDS Research and Human Retroviruses, vol. 10, No. 5, pp. 607–616 (Nov. 5, 1994).

Gibbs et al. "Progression to AIDS in the Absence of a Gene for vpr or vpx," J. Virol., vol. 69, No. 4, pp. 2378–2383 (Apr. 1995).

Guyader et al. "VPX mutants of HIV–2 are infectious in established cell lines but display a severe defect in peripheral blood lymphocytes," The EMBO Journal, vol. 8, No. 4, pp. 1169–1175 (1989).

Zhao et al. "Biochemical Mechanism of HIV–1 Vpr Function: Oligomerization Mediated by the N–Terminal Domain," J. Biol. Chem. 269, pp. 32131–32137 (Dec. 1994).

He et al. "Human Immunodeficiency Virus Type 1 Viral Protein R (Vpr) Arrests Cells in the $G_2$ Phase of the Cell Cycle by Inhibiting p34$^{cdc2}$ Activity," J. Virol., vol. 69, No. 11, pp. 6705–6711 (Nov. 1995).

Heinzinger et al. "The Vpr protein of human immunodeficiency virus type 1 influences nuclear localization of viral nucleic acids in nondividing host cells," Proc. Natl. Acad. Sci. USA, vol. 91, pp. 7311–7315 (Jul. 1994).

Hoch et al. "vpr Deletion Mutant of Simian Immunodeficiency Virus Induces AIDS in Rhesus Monkeys," J. Virol., vol. 69, No. 8, pp. 4807–4813 (Aug. 1995).

Horton et al. "HIV–2 Viral Protein X Association with the Gag p27 Capsid Protein," Virology 199, 453–457 (1994).

Kewalramani et al. "Vpx Association with Mature Core Structures of HIV–2," Virology 218, 159–168 (1996).

Kewalramani et al. "Protein Stability Influences Human Immunodeficiency Virus Type 2 Vpr Virion Incorporation and Cell Cycle Effect," Virology 218, 326–334 (1996).

Kirchhoff et al. "Upstream U3 Sequences in Simian Immunodeficiency Virus Are Selectively Deleted In Vivo in the Absence of an Intact nef Gene," J. Virol., vol. 68, No. 3, pp. 2031–2037 (Mar. 1994).

Kondo et al. "The p6$^{gag}$ Domain of Human Immunodeficiency Virus Type 1 Is Sufficient for the Incorporation of Vpr into Heterologous Viral Particles," J. Virol., vol. 69, No. 5, pp. 2759–2764 (May 1995).

Lang et al. "Importance of vpr for Infection of Rhesus Monkeys with Simian Immunodeficiency Virus," J. Virol., vol. 67, No. 2, pp. 902–912 (Feb. 1993).

Lavallée et al. "Requirement of the Pr55$^{gag}$ Precursor for Incorporation of the Vpr Product into Human Immunodeficiency Virus Type 1 Viral Particles," J. Virol., vol. 68, No. 3, pp. 1926–1934 (Mar. 1994).

Levy et al. "Extracellular Vpr Protein Increases Cellular Permissiveness to Human Immunodeficiency Virus Replication and Reactivates Virus from Latency," J. Virol., vol. 69, No. 2, pp. 1243–1252 (Feb. 1995).

Levy et al. "Induction of Cell Differentiation by Human Immunodeficiency Virus 1 vpr," Cell, vol. 72, 541–550 (Feb. 26, 1993).

Levy et al. "Serum Vpr regulates productive infection and latency of human immunodeficiency virus type 1," Proc. Natl. Acad. Sci. USA, vol. 91, pp. 10873–10877 (Nov. 1994).

Lu et al. "A Leucine Triplet Repeat Sequence (LXX)$_4$ in p6$^{gag}$ Is Important for Vpr Incorporation into Human Immunodeficiency Virus Type 1 Particles," J. Virol., vol. 69, No. 11, pp. 6873–6879 (Nov. 1995).

Lu et al. "Human Immunodeficiency Virus Type 1 Viral Protein R Localization in Infected Cells and Virions," J. Virol., vol. 67, No. 11, pp. 6542–6550 (Nov. 1993).

Macreadie et al. "A domain of human immunodeficiency virus type 1 Vpr containing repeated H(S/F)RIG amino acid motifs causes cell growth arrest and structural defects," Proc. Natl. Acad. Sci. USA, vol. 92, pp. 2770–2774 (Mar. 1995).

Mahalingam et al. "The Carboxy–Terminal Domain Is Essential for Stability and Not for Virion Incorporation of HIV–1 Vpr into Virus Particles," Virology 214, 647–652 (1995).

Mahalingam et al. "Functional Analysis of HIV–1 Vpr: Identification of Determinants Essential for Subcellular Localization," Virology 212, 331–339 (1995).

Mahalingam et al. "HIV–1 Vpr interacts with a human 34kDa mov34 homologue, a cellular factor linked to the $G_2$/M phase transition of the mammalian cell cycle," Proc. Natl. Acad. Sci. USA, vol. 95, pp. 3419–3424 (1998).

Mahalingam et al. "Identification of Residues in the N–Terminal Acidic Domain of HIV–1 Vpr Essential for Virion Incorporation," Virology 207, 297–302 (1995).

Marcon et al. "Dispensable Role of the Human Immunodeficiency Virus Type 2 Vpx Protein in Viral Replication," J. Virol., vol. 65, No. 7, pp. 3938–3942 (Jul. 1991).

Marcon et al. "Functional Studies of the HIV–2 VPX Protein," p. 310 (Abstract).

Matsuda et al., "A virion–specific inhibitory molecule with therapeutic potential for human immunodeficiency virus type 1," Proc. Natl. Acad. Sci. USA, vol. 90, pp. 3544–3548 (Apr. 1993).

Ogawa et al. "Mutational Analysis of the Human Immunodeficiency Virus vpr Open Reading Frame," J. Virol., vol. 63, No. 9, pp. 4110–4114 (Sep. 1989).

Shibata et al. "Construction and Characterization of an Infectious DNA Clone and of Mutants of Simian Immunodeficiency Virus Isolated from the African Green Monkey," J. Virol., vol. 64, No. 1, pp. 307–312 (Jan. 1990).

Shibata et al. "Generation of a Chimeric Human and Simian Immunodeficiency Virus Infectious to Monkey Peripheral Blood Mononuclear Cells," J. Virol., vol. 65, No. 7, pp. 3514–3520 (Jul. 1991).

Shibata et al. "Mutational Analysis of the Human Immunodeficiency Virus Type 2 (HIV–2) Genome in Relation to HIV–1 and Simian Immunodeficiency Virus $SIV_{AGM}$," J. Virol., vol. 64, No. 2, pp. 742–747 (Feb. 1990).

Trono. "HIV Accessory Proteins: Leading Roles for the Supporting Cast," Cell, vol. 82, 189–192 (Jul. 28, 1995).

Wang et al. "Particle assembly and Vpr expression in human immunodeficiency virus type 1–infected cells demonstrated by immunoelectron microscopy," Journal of General Virology, vol. 75, pp. 2607–2614 (1994).

Westervelt et al. "Dual Regulation of Silent and Productive Infection in Monocytes by Distinct Human Immunodeficiency Virus Type 1 Determinants," J. Virol., vol. 66, No. 6, pp. 3925–3931 (Jun. 1992).

Park et al. "Amino Acid Sequence Requirements for the Incorporation of the Vpx Protein of Simian Immunodeficiency Virus into Virion Particles," J. Acq. Immune Def. Synd., 10:506–510 (1995).

Park et al. "Targeting a foreign protein into virion particles by fusion with the Vpx protein of simian immunodeficiency virus," J. Acq. Immune Def. Synd., 11(4):341–50 (Apr. 1, 1996).

Paxton et al. "Incorporation of Vpr into Human Immunodeficiency Virus Type 1 Virions: Requirement for the p6 Region of gag and Mutational Analysis," J. Virol., vol. 67, No. 12, pp. 7229–7237 (Dec. 1993).

Rogel et al. "The Human Immunodeficiency Virus Type 1 vpr Gene Prevents Cell Proliferation during Chronic Infection," J. Virol., vol. 69, No. 2, pp. 882–888 (Feb. 1995).

Re et al. "Human Immunodeficiency Virus Type 1 Vpr Arrests the Cell Cycle in $G_2$ by Inhibiting the Activation of $p34^{cdc2}$–Cyclin B," J. Virol., vol. 69, No. 11, pp. 6859–6864 (Nov. 1995).

Sato et al. "Targeting of Chrolamphenicol Acetyltransferase to Human Immunodeficiency Virus Particles via Vpr and Vpx," Microbiol. Immunol., 39(12), 1015–1019 (1995).

Wong–Staal et al. "Human Immunodeficiency Virus: The Eighth Gene," Aids Research and Human Retroviruses, vol. 3, No. 1 (1987).

Yao et al. "Mutagenic Analysis of Human Immunodeficiency Virus Type 1 Vpr: Role of a Predicted N–Terminal Alpha–Helical Structure in Vpr Nuclear Localization and Virion Incorporation," J. Virol. vol. 69, No. 11, pp. 7032–7044 (Nov. 1995).

Yu et al. "Open Reading Frame vpr of Simian Immunodeficiency Virus Encodes a Virion–Associated Protein," J. Virol., vol. 64, No. 11, pp. 5688–5693 (Nov. 1990).

Yu et al. "The vpx Gene of Simian Immunodeficiency Virus Facilitates Efficient Viral Replication in Fresh Lymphocytes and Macrophages," J. Virol., vol. 65, No. 9, pp. 5088–5091 (Sep. 1991).

Yu et al. "Vpx of Simian Immunodeficiency Virus Is Localized Primarily Outside the Virus Core in Mature Virions," J. Virol., vol. 67, No. 7, pp. 4386–4390 (Jul. 1993).

Yuan et al. "Human Immunodeficiency Virus vpr Gene Encodes a Virion–Associated Protein," AIDS Research and Human Retroviruses, vol. 6, No. 11, pp. 1265–1271 (1990).

Hattori et al. "The human immunodeficiency virus type 2 vpr gene is essential for productive infection of human macrophages," Proc. Natl. Acad. Sci. USA, vol. 87, pp. 8080–8084 (Oct. 1990).

Hattori et al. "The HIV–2 Vpr Gene is Essential for Macrophage Infections," p. 309 (Abstract).

A vpr1SN (ug DNA): 10  10   5   2.5      2.5  5   10       0   0   0
vpr1 (ug DNA):    2.5  5  10  10        0   0    0      2.5  5  10

Vpr1SN →

Vpr1 →

B vpx2SN (ug DNA) 10  10   5   2.5      2.5  5   10       0   0   0
vpx2 (ug DNA)   2.5  5  10  10         0   0    0      2.5  5  10

Vpx2SN →

Vpx2 →

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 27
        (B) TYPE: nucleic acid
        (C) STRANDEDNESS: double
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:1:

GCCACCTTTG TCGACTGTTA AAAAACT                              27

(2) INFORMATION FOR SEQ ID NO:2:

(i) SEQUENCE CHARACTERISTICS:

-continued

```
        (A) LENGTH: 24
        (B) TYPE: nucleic acid
        (C) STRANDEDNESS: double
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:2:

GTCCTAGGCA  AGCTTCCTGG  ATGC                                             24

(2) INFORMATION FOR SEQ ID NO:3:

(i) SEQUENCE CHARACTERISTICS:
        (A) LENGTH: 25
        (B) TYPE: nucleic acid
        (C) STRANDEDNESS: double
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:3:

AAGGAGAGCC  ATGGGTGCGA  GAGCG                                            25

(2) INFORMATION FOR SEQ ID NO:4:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE:
        (A) DESCRIPTION: other nucleic acid (iii) HYPOTHETICAL: No (iv) ANTI-SENSE: Yes (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:4:

GGGGATCCCT  TTATTGTGAC  GAGGGG                                           26
```

```
(2) INFORMATION FOR SEQ ID NO:5:

(i) SEQUENCE CHARACTERISTICS:
        (A) LENGTH: 25
        (B) TYPE: nucleic acid
        (C) STRANDEDNESS: double
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:5:

ATTGTGGGCC ATGGGCGCGA GAAAC                                       25

(2) INFORMATION FOR SEQ ID NO:6:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE:
        (A) DESCRIPTION: other nucleic acid (iii) HYPOTHETICAL: No (iv) ANTI-SENSE: Yes (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:6:

GGGGGGCCCC TACTGGTCTT TTCC                                        24

(2) INFORMATION FOR SEQ ID NO:7:

(i) SEQUENCE CHARACTERISTICS:
        (A) LENGTH: 28
        (B) TYPE: nucleic acid
        (C) STRANDEDNESS: double
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:
```

(xi) SEQUENCE DESCRIPTION: SEQ ID NO:7:

GAAGATCTAC CATGGAAGCC CCAGAAGA                                    28

(2) INFORMATION FOR SEQ ID NO:8:

(i) SEQUENCE CHARACTERISTICS:
           (A) LENGTH: 39
           (B) TYPE: nucleic acid
           (C) STRANDEDNESS: double
           (D) TOPOLOGY: linear (ii) MOLECULE TYPE:
           (A) DESCRIPTION: other nucleic acid (iii) HYPOTHETICAL: No (iv) ANTI-SENSE: Yes (vi) ORIGINAL SOURCE:
           (B) STRAIN:
           (C) INDIVIDUAL ISOLATE:
           (D) DEVELOPMENTAL STAGE:
           (F) TISSUE TYPE:
           (G) CELL TYPE:
           (H) CELL LINE:

(xi) SEQUENCE DESCRIPTION: SEQ ID NO:8:

CGCGGATCCG TTAACATCTA CTGGCTCCAT TTCTTGCTC                         39

(2) INFORMATION FOR SEQ ID NO:9:

(i) SEQUENCE CHARACTERISTICS:
           (A) LENGTH: 25
           (B) TYPE: nucleic acid
           (C) STRANDEDNESS: double
           (D) TOPOLOGY: linear (ii) MOLECULE TYPE:
           (A) DESCRIPTION: other nucleic acid (iii) HYPOTHETICAL: No (iv) ANTI-SENSE: No (vi) ORIGINAL SOURCE:
           (B) STRAIN:
           (C) INDIVIDUAL ISOLATE:
           (D) DEVELOPMENTAL STAGE:
           (F) TISSUE TYPE:
           (G) CELL TYPE:
           (H) CELL LINE:

(xi) SEQUENCE DESCRIPTION: SEQ ID NO:9:

GTGCAACACC ATGGCAGGCC CCAGA                                       25

(2) INFORMATION FOR SEQ ID NO:10:

(i) SEQUENCE CHARACTERISTICS:
           (A) LENGTH: 39
           (B) TYPE: nucleic acid
           (C) STRANDEDNESS: double
           (D) TOPOLOGY: linear (ii) MOLECULE TYPE:
           (A) DESCRIPTION: other nucleic acid (iii) HYPOTHETICAL: No (iv) ANTI-SENSE: Yes (vi) ORIGINAL SOURCE:
           (B) STRAIN:
           (C) INDIVIDUAL ISOLATE:
           (D) DEVELOPMENTAL STAGE:

```
        (F) TISSUE TYPE:
        (G) CELL TYPE:
        (H) CELL LINE:

(xi) SEQUENCE DESCRIPTION: SEQ ID NO:10:

TGCACTGCAG   GAAGATCTTA   GACCTGGAGG   GGGAGGAGG                                39
```

FUSION PROTEIN DELIVERY SYSTEMS AND USES THEREOF

This is a file wrapper continuation of application Ser. No. 08/421,982 filed Apr. 14, 1995, now abandoned.

BACKGROUND OF THE INVENTION

1. Field of the Invention

The present invention relates generally to the fields of molecular virology and protein chemistry. More specifically, the present invention relates to the use of Human and Simian Immunodeficiency Virus (HIV/SIV) Vpx and Vpr proteins, or amino acid residues that mediate their packaging, as vehicles for delivery of proteins/peptides to virions or virus-like particles and uses thereof.

2. Description of the Related Art

Unlike simple retroviruses, human and simian immunodeficiency viruses (HIV/SIV) encode proteins in addition to Gag, Pol, and Env that are packaged into virus particles. These include the Vpr protein, present in all primate lentiviruses, and the Vpx protein, which is unique to the HIV-2/SIV$_{SM}$/SIV$_{MAC}$ group of viruses. Since Vpr and Vpx are present in infectious virions, they have long been thought to play important roles early in the virus life cycle. Indeed, recent studies of HIV-1 have shown that Vpr has nucleophilic properties and that it facilitates, together with the matrix protein, nuclear transport of the viral preintegration complex in nondividing cells, such as the macrophage. Similarly, Vpx-deficient HIV-2 has been shown to exhibit delayed replication kinetics and to require 2–3 orders of magnitude more virus to produce and maintain a productive infection in peripheral blood mononuclear cells. Thus, both accessory proteins appear to be important for efficient replication and spread of HIV/SIV in primary target cells.

Incorporation of foreign proteins into retrovirus particles has previously been reported by fusion with gag. Using the yeast retrotransposon Ty1 as a retrovirus assembly model, Natsoulis and Boeke tested this approach as a novel means to interfere with viral replication. More recently, the expression of a murine retrovirus capsid-staphylococcal nuclease fusion protein was found to inhibit murine leukemia virus replication in tissue culture cells.

The prior art lacks effective means of delivering or targeting foreign, e.g., toxic proteins to virions. The present invention fulfills this longstanding need and desire in the art.

SUMMARY OF THE INVENTION

Vpr and Vpx packaging is mediated by the Gag precursor and thus must play an important role in HIV assembly processes.

The present invention shows that Vpr and Vpx can be used as vehicles to target foreign proteins to HIV/SIV virions. Vpr1 and Vpx2 gene fusions were constructed with the bacterial staphylococcal nuclease (SN) and chloramphenicol acetyl transferase (CAT) genes. Unlike Gag or Pol proteins, Vpr and Vpx are dispensable for viral replication in immortalized T-cell lines. Thus, structural alteration of these accessory proteins may be more readily tolerated than similar changes in Gag or Gag/Pol. Fusion proteins containing a Vpx or Vpr moiety should be packaged into HIV particles by expression in trans, since their incorporation should be mediated by the same interactions with Gag that facilitates wild-type Vpr and Vpx protein packaging.

Vpr and Vpx fusion proteins were constructed and their abilities to package into HIV particles were demonstrated. Fusion partners selected for demonstration were: staphylococcal nuclease because of its potential to degrade viral nucleic acid upon packaging and the chloramphenicol acetyl transferase because of its utility as a functional marker. To control for cytotoxicity, an enzymatically inactive nuclease mutant (SN*), derived from SN by site-directed mutagenesis was also used. This SN* mutant differs from wild-type SN by two amino acid substitutions; Glu was changed to Ser (position 43) and Arg was changed to Gly (position 87). SN* folds normally, but has a specific activity that is $10^6$-fold lower than wild-type SN. Using transient expression systems and in trans complementation approaches, fusion protein stability, function and packaging requirements was shown. The present invention shows that Vpr1 and Vpx2 fusion proteins were expressed in mammalian cells and were incorporated into HIV particles even in the presence of wild-type Vpr and/or Vpx proteins. Most importantly, however, the present invention shows that virion incorporated Vpr and Vpx fusions remain enzymatically active. Thus, targeting heterologous Vpr and Vpx fusion proteins, including deleterious enzymes, to virions represents a new avenue toward anti-HIV drug discovery.

In one embodiment of the present invention, there is provided a composition of matter, comprising: DNA encoding a viral Vpx protein fused to DNA encoding a virus inhibitory protein.

In another embodiment of the present invention, there is provided a composition of matter, comprising: DNA encoding a viral Vpr protein fused to DNA encoding a virus inhibitory protein.

In yet another embodiment of the present invention, there is provided a method of delivering a virus inhibitory molecule to a target in an animal, comprising the step of administering to said animal an effective amount of the composition of the present invention.

In still yet another embodiment of the present invention, there is provided a pharmaceutical composition, comprising a composition of the present invention and a pharmaceutically acceptable carrier.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A shows the illustration of the pTM-vpr1 expression plasmid. The HIV-1$_{YU2}$ vpr coding region was amplified by PCR and ligated into pTM1 at the NcoI and BamHI restriction sites. FIG. 1B shows the illustration of the pTM-vpx2 expression plasmid. The HIV-2$_{ST}$ vpx coding region was amplified by PCR and ligated into pTM1 at the NcoI and BglII/SmaI sites. FIG. 1C shows the illustration of the fusion junctions of the pTM-vpr1SN/SN* expression plasmids. SmaI/XhoI DNA fragments containing SN and SN* were ligated into HpaI/XhoI cut pTM-vpr1. Blunt-end ligation at HpaI and SmaI sites changes the vpr translational stop codon (TAA) to Trp and substituted the C terminal Ser with a Cys residue. FIG. 1D shows the illustration of the fusion junctions of the pTM-vpx2SN/SN* expression plasmids. BamHI/XhoI DNA fragments containing SN and SN* were ligated into BamHI/XhoI cut pTM-vpx2. In the construction of these plasmids, the Vpx C terminal Arg codon was changed to a Val codon and a Ser residue was introduced in place of the Vpx translational stop codon (TAA). Fusion of vpx and SN/SN* at the BamHI sites left a short amino acid sequence of the pTM1 polylinker (double underlined) between the two coding regions.

FIG. 2A shows the pTM1, pTM-vpr1, pTM-vpr1SN and pTM-vpr1SN* were transfected into HeLa cells one hour after infection with rVT7 (MOI=10). Twenty-four hours later cell lysates were prepared and examined by immunoblot analysis. Replica blots were probed with anti-Vpr1 (left) and anti-SN (right) antibodies. FIG. 2B shows that replica blots, prepared from rVT7 infected HeLa cells transfected with pTM1, pTM-vpx2, pTM-vpx2SN and pTM-vpx2SN*, were probed with anti-Vpx2 (left) and anti-SN (right) antibodies. Bound antibodies were detected by ECL (Amersham) methods as described by the manufacturer.

FIG. 3A transfection of T7 expressing (rVT7 infected) HeLa cells with pTM-vpr1, pTM-vpr1SN, and pTM-vpr1SN* alone and in combination with pTM-gag1. pTM1 was also transfected for control. Culture supernatant were collected twenty-four hours after transfection, clarified by centrifugation (1000×g, 10 min.) and ultracentrifuged (125,000×g, 2 hrs.) over cushions of 20% sucrose. Pellets (VLPs, middle and bottom panels) and cells (top panel) were solubilized in loading buffer and examined by immunoblot analysis using anti-Vpr1 (top and middle) and anti-Gag (bottom) antibodies as probes. FIG. 3B transfection of T7 expressing HeLa cells pTM-vpx2, pTM-vpx2SN and pTM-vpx2SN* alone and in combination with pTM-gag2. Pellets (VLPs, middle and bottom panels) and cells (top panel) were lysed, proteins were separated by SDS-PAGE and electroblotted blotted to nitrocellulose as described above. Replica blots were probed with anti-Vpx2 (top and middle panels) and anti-Gag (bottom panel) antibodies. Bound antibodies were detected using ECL methods.

FIG. 4A shows that HIV-1 Gag mediates packaging of Vpr1SN. rVT7 infected (T7 expressing) HeLa cells were transfected with pTM-vpr1SN alone and in combination with pTM-gag2 and pTM-gag1. Pellets (VLPs, middle and bottom panels) and cells (top panel) were prepared 24 hours after transfection and examined by immunoblot analysis using anti-Vpr1 (top and middle) and anti-Gag (bottom) antibodies for probes. (B) HIV-2 Gag mediates packaging of Vpx2SN. T7 expressing HeLa cells were transfected with pTM-vpx2SN alone and in combination with pTM-gag1 and pTM-gag2. Pellets (VLPs, middle and bottom panels) and cells (top panel) were prepared 24 hours after transfection and examined by immunoblot analysis using anti-Vpx2 (top and middle) and anti-Gag (bottom) antibodies for probes.

FIG. 5A shows transfection of T7 expressing HeLa cells with different amounts of pTM-vpr1 (2.5, 5 and 10 ug) and pTM-vpr1SN (2.5, 5 and 10 ug), either individually or together in combination with pTM-gag1 (10 ug). FIG. 5B shows that HeLa cells were transfected with different amounts of pTM-vpx2 (2.5, 5 and 10 ug) and pTM-vpx2SN (2.5, 5 and 10 ug), either individually or together with pTM-gag2 (10 ug). Twenty hours after transfection, particles were concentrated by ultracentrifugation through sucrose cushions and analyzed by immunoblotting using anti-Vpr1 (A) or anti-Vpx2 (B) antibodies.

FIG. 7A shows the construction of the pLR2P-vpx2SN/S expression plasmids. To facilitate efficient expression of HIV genes, the HIV-2 LTR and RRE were engineered into the polylinker of pTZ19U, generating pLR2P. The organization of these elements within the pTZ19U polylinker is illustrated. NcoI/XhoI vpx2SN and vpx2SN* (vpxSN/SN*) containing DNA fragments were ligated into pLR2P, generating pLR2P-vpx2SN and pLR2P-vpx2SN* (pLR2P-vpxSN/SN*). FIG. 7B shows the association of Vpx2SN with HIV-2 virions. Monolayer cultures of HLtat cells were transfected with HIV-2ST proviral DNA (pSXB 1) and cotransfected with pSXB1/pTM-vpx2SN and pSXB1/pTM-vpx2SN*. Extracellular virus was concentrated from culture supernatants forty eight hours after transfection by ultracentrifugation (125,000×g, 2 hrs.) through cushions of 20% sucrose. Duplicate Western blots of viral pellets were prepared and probed independently with anti-Vpx2 (left) anti-SN (middle) and anti-Gag (right) antibodies. FIG. 7C shows a sucrose gradient analysis. Pellets of supernatant-virus prepared from pSXB1/pTM-vpx2SN cotransfected HLtat cells were resuspended in PBS, layered over a 20–60% linear gradient of sucrose and centrifuged for 18 hours at 125,000×g. Fractions (0.5 ml) were collected from the bottom of the tube, diluted 1:3 in PBS, reprecipitated and solubilized in electrophoresis buffer for immunoblot analysis. Replica blots were probed with anti-SN (top) and anti-Gag (bottom) antibodies. Fraction 1 represents the first collection from the bottom of the gradient and fraction 19 represents the last collection. Only alternate fractions are shown, except at the peak of protein detection. FIG. 7D shows the incorporation of Vpx2SN into HIV-$2_{7312A}$ Vpr and Vpx competent virus. Virus concentrated from supernatants of HLtat cells transfected with HIV-$2_{7312A}$ proviral DNA (pJK) or cotransfected with pJK/pLR2P-vpx2SN or pJK/pLR2P-vpx2SN* was prepared for immunoblot analysis as described above. Included for control were virions derived by pSXB1/pLR2P-vpx2SN* cotransfection. Duplicate blots were probed with anti-Vpx (left) and anti-Gag (right) antibodies.

Figure 1:
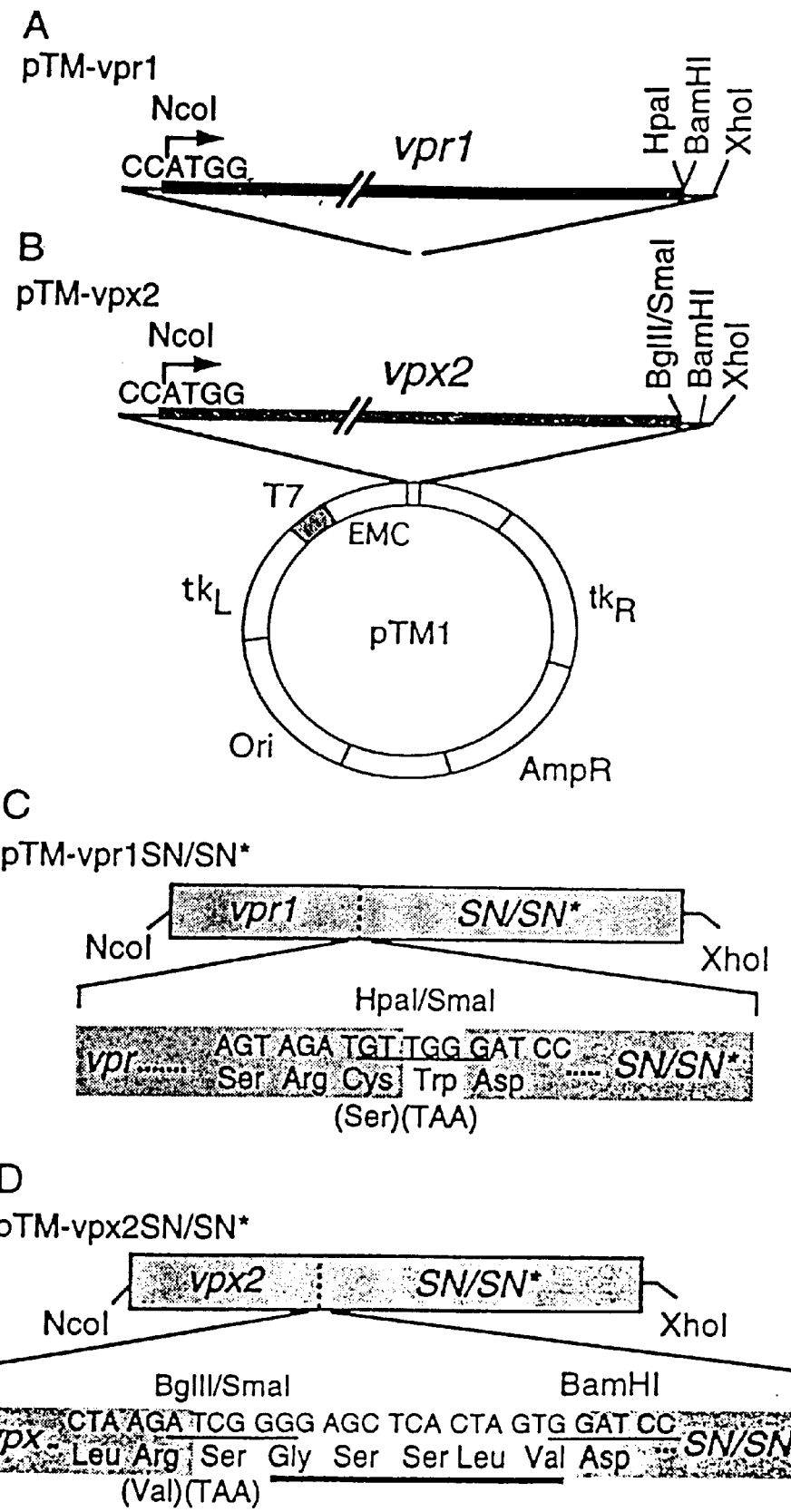
FIGS. 1A–1D show the construction of vpr1, vpr1SN/SN*, vpx 2 and vpx2SN/SN* expression plasmids.

The following examples are given for the purpose of illustrating various embodiments of the invention and are not meant to limit the present invention in any fashion.

EXAMPLE 1

Cells and Viruses

HeLa, HeLa-tat (HLtat) and CV-1 cells were maintained in Dulbecco's Modified Eagle's Medium supplemented with 10% fetal bovine serum (FBS). HLtat cells constitutively express the first exon of HIV-1 tat and were provided by Drs. B. Felber and G. Pavlakis. A recombinant vaccinia virus (rVT7) containing the bacteriophage T7 RNA polymerase gene was used to facilitate expression of viral genes placed under the control of a T7 promoter. Stocks of rVT7 were prepared and titrated in CV-1 cells as described previously by Wu, et al., *J. Virol.* 66:7104–7112 (1992). HIV-1$_{YU2}$, HIV-1 pNL 4-3-R⁻ and pNL 4-3, HIV-1$_{HXB2D}$, HIV-2$_{ST}$, and HIV-2$_{7312A}$ proviral clones were used for the construction of recombinant expression plasmids and the generation of transfection derived viruses.

EXAMPLE 2

Antibodies

To generate HIV-1 Vpr specific antibodies, the HIV-1$_{YU-2}$ vpr open reading frame was amplified by polymerase chain reaction (PCR) using primers (sense: 5'-GCCACCTTTGTCGACTGTTAAAAAACT-3' SEQ ID NO.1 and anti-sense: 5'-GTCCTAGGCAAGCTTCCTGGATGC-3'SEQ ID NO. 2) containing SalI and HindIII sites and ligated into the prokaryotic expression vector, pGEX, generating pGEX-vpr1. This construct allowed expression of Vpr1 as a C terminal fusion protein with glutathione S-transferase (gst), thus allowing protein purification using affinity chromatography. *E. coli* (DH5a) were transformed with pGEX-vpr1 and protein expression was induced with isopropyl β-D thiogalactopyranoside (IPTG). Expression of the gst-Vpr1 fusion protein was confirmed by SDS-PAGE. Soluble gst-Vpr1 protein was purified and Vpr1 was released by thrombin cleavage using previously described procedures of Smith, et al., *Gene* 67:31–40 (1988). New Zealand White rabbits were immunized with 0.4 mg of purified Vpr1 protein emulsified 1:1 in Freunds complete adjuvant, boosted three times at two week intervals with 0.25 mg of Vpr1 mixed 1:1 in Freunds' incomplete adjuvant and bled eight and ten weeks after the first immunization to collect antisera. Additional antibodies used included monoclonal antibodies to HIV-1 Gag (ACT1, and HIV-2 Gag (6D2.6), polyclonal rabbit antibodies raised against the HIV-2 Vpx protein and anti-SN antiserum raised against purified bacterially expressed SN protein.

EXAMPLE 3

Construction of T7-based expression plasmids

A DNA fragment encompassing HIV-1$_{HXB2D}$ gag (nucleotides 335–1837) was amplified by PCR using primers (sense: 5'-AAGGAGAGCCATGGGTGCGAGAGCG-3' SEQ ID NO.3 and anti-sense: 5'GG GGATCCCTTTATTGTGACGAGGGG-3' SEQ ID NO.4) containing NcoI and BamHI restriction sites, respectively (underlined). The PCR product was digested with NcoI and BamHI, purified and ligated into the polylinker of the pTM1 vector, generating pTM-gag1. Similarly, a DNA fragment containing the gag coding region of HIV-2ST (nucleotides 547–2113) was amplified by PCR using sense and anti-sense primers 5'-ATTGTGGGCCATGGGGCGCGAGAAAC-3' SEQ ID NO.5 and 5'-GGG GGGCCCCTACTGGTCTTTTCC-3' SEQ ID NO.6, respectively. The reaction product was cut with NcoI and SmaI (underlined), purified and ligated into the polylinker of pTM1, generating pTM-gag2.

For expression of Vpr1 under the control of the T7 promoter, a DNA fragment containing the HIV-1$_{YU2}$ vpr coding region (nucleotides 5107–5400) was amplified by PCR using primers (sense: 5'-GAAGATCTA CCATGGAAGCCCCAGAAGA-3' SEQ ID NO.7 and anti-sense: 5'-CGC GGATCCGTTAACATCTACTGGCTCCATTTCTTGCTC-3' SEQ ID NO.8) containing NcoI and HpaI/BamHI sites, respectively (underlined). The reaction product was cut with NcoI and BamHI and ligated into pTM1, generating pTM-vpr1 (FIG. 1A). In order to fuse SN and SN* in-frame with vpr1, their coding regions were excised from pGN1561.1 and pGN1709.3, respectively and through a series of subcloning steps, ligated into the SmaI/XhoI sites of pTM-vpr1, generating pTM-vpr1SN and pTM-vpr1SN*. This approach changed the translational stop codon of Vpr1 to a Trp codon and the C terminal Ser residue to a Cys. The resulting junctions between vpr1 and SN/SN* are depicted in FIG. 1C.

For expression of Vpx2 under T7 control, a DNA fragment containing the HIV-2ST vpx coding sequence (nucleotides 5343–5691) was amplified by PCR using primers (sense: 5'-GTGCAACACCATGGCAGGCCCCAGA-3' SEQ ID NO.9 and anti-sense: 5'-TGCACTGCAGGA AGATCTTAGACCTGGAGGGGGAGGAGG-3' SEQ ID NO.10) containing NcoI and BglII sites, respectively (underlined). After cleavage with BglII and Klenow fill-in, the PCR product was cleaved with NcoI, purified and ligated into the NcoI and SmaI sites of pTM1, generating pTM-vpx2 (FIG. 1B). To construct in-frame fusions with vpx2, BamHI/XhoI, SN- and SN* -containing DNA fragments were excised from pTM-vpr1SN and pTM-vpr1SN* and ligated into pTM-vpx2, generating pTM-vpx2SN and pTM-vpx2SN*, respectively. This approach introduced one amino acid substitution at the C terminus of Vpx (Val to Arg), changed the translational stop codon of vpx to Ser and left five amino acids residues of the pTM1 plasmid polylinker.

The resulting junctions between vpx2 and SN/SN* are depicted in FIG. 1D.

EXAMPLE 4

Construction of HIV LTR-based expression plasmids

Figure 7:
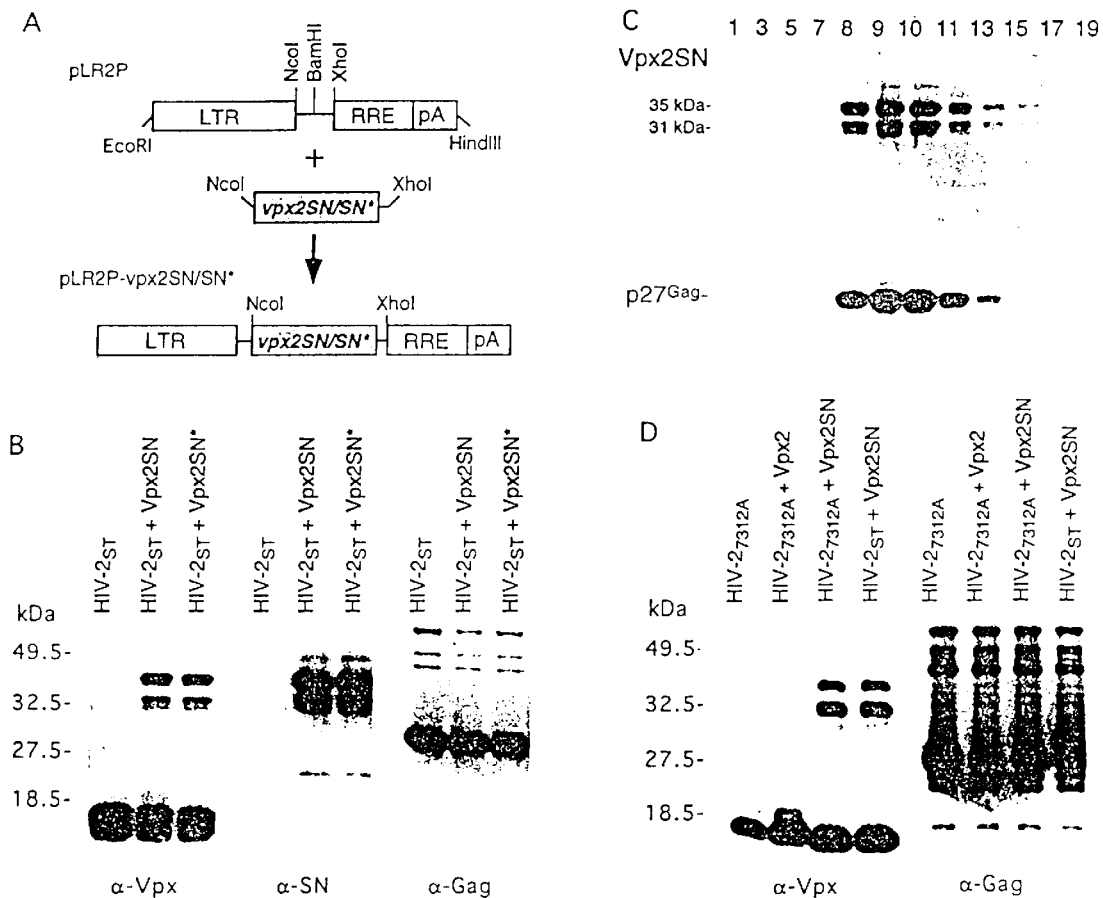
FIGS. 7A–7D show the incorporation of Vpx2SN into HIV-2 by trans complemention.
Figure 9:
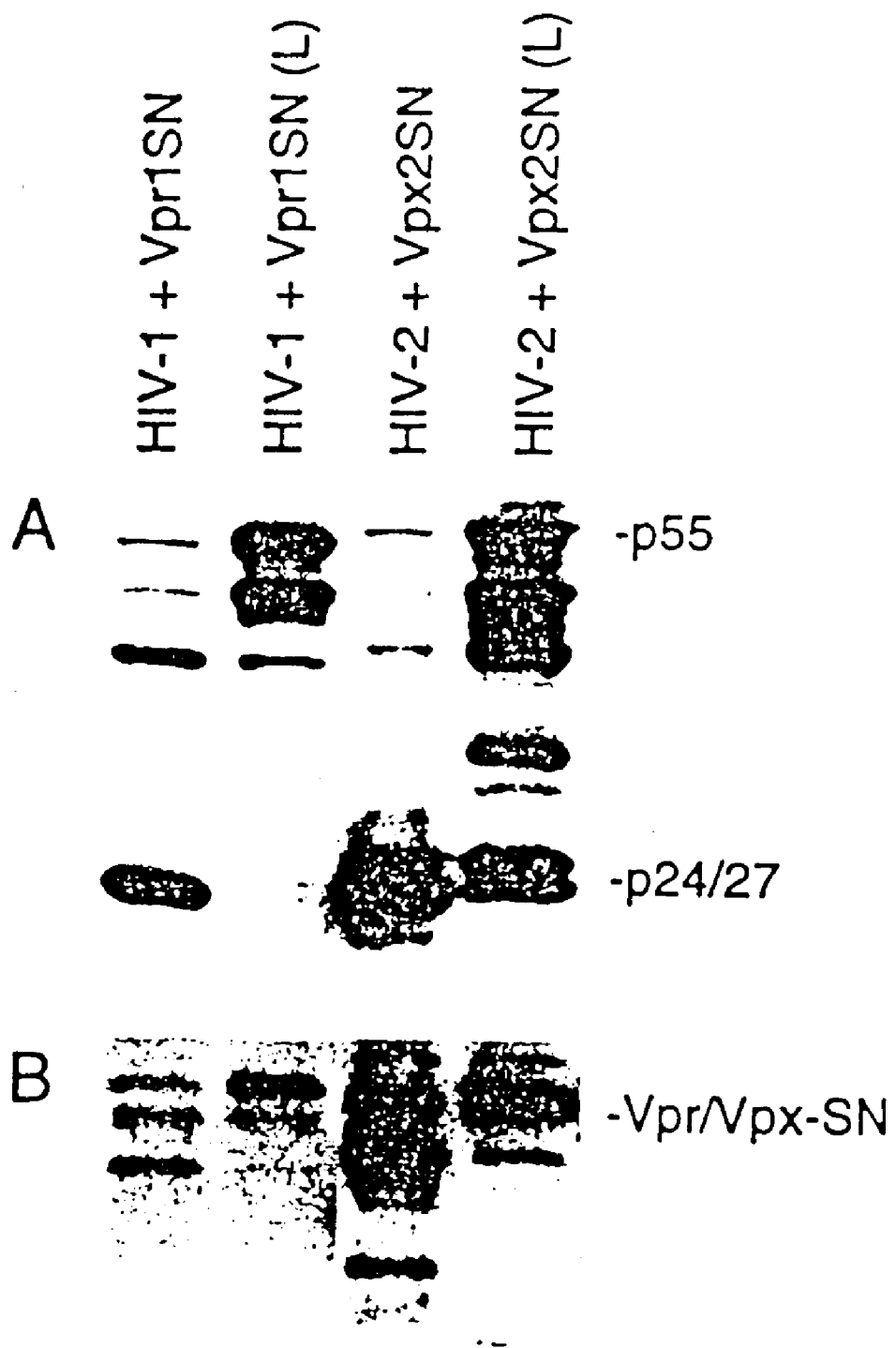

For efficient expression of Vpr and Vpx fusion proteins in the presence HIV, a eukaryotic expression vector (termed pLR2P) was constructed which contains both an HIV-2 LTR (HIV-2$_{ST}$, coordinates −544 to 466) and an HIV-2 RRE (HIV-2$_{ROD}$, coordinates 7320 to 7972) element (FIG. 7A). These HIV-2 LTR and RRE elements were chosen because they respond to both HIV-1 and HIV-2 Tat and Rev proteins. The vpr1, vpr1SN, vpx2 and vpx2SN coding regions were excised from their respective pTM expression plasmids (see FIG. 1) with NcoI and XhoI restriction enzymes and ligated into pLR2P, generating pLR2P-vpr1, pLR2P-vpr1SN, pLR2P-vpx2 and pLR2P-vpx2SN, respectively (FIG. 7A). For construction and expression of vpr- and vpx- CAT gene fusions, the SN containing regions (BamHI/XhoI fragments) of pLR2P-vpr1SN and pLR2P-vpx2SN were removed and substituted with a PCR amplified BglII/XhoI DNA fragment containing CAT, generating pLR2P-vpr1CAT and pLR2P-vpx2CAT, respectively (FIG. 9A).

EXAMPLE 5

Transfections

Transfections of proviral clones were performed in HLtat cells using calcium phosphate DNA precipitation methods as described by the manufacturer (Stratagene). T7-based (pTM1) expression constructs were transfected using Lipofectin (BioRad) into rVT7 infected HeLa cells as described previously by Wu, et al., *J. Virol.* 68:6161–6169 (1994). These methods used were those recommended by the manufacturer of the Lipofectin reagent

EXAMPLE 6

Western immunoblot analysis

Virions and virus-like particles (VLPs) were concentrated from the supernatants of transfected or infected cells by ultracentrifugation through 20% cushions of sucrose (125,000×g, 2 hrs., 4° C.). Pellets and infected/transfected cells were solubilized in loading buffer [62.5 mM Tris-HCl (pH 6.8) 0.2% sodium lauryl sulfate (SDS), 5% 2-mercaptoethanol, 10% glycerol], boiled and separated on 12.5% polyacrylamide gels containing SDS. Following electrophoresis, proteins were transferred to nitrocellulose (0.2 μm; Schleicher & Schuell) by electroblotting, incubated for one hour at room temperature in blocking buffer (5% nonfat dry milk in phosphate buffered saline [PBS]) and then for two hours with the appropriate antibodies diluted in blocking buffer. Protein bound antibodies were detected with HRP-conjugated specific secondary antibodies using ECL methods according to the manufacturer's instructions (Amersham).

EXAMPLE 7

SN nuclease activity assay

Cells and viral pellets were resuspended in nuclease lysis buffer (40 mM Tris-HCl, pH 6.8, 100 mM NaCl, 0.1% SDS, 1% Triton X-100) and clarified by low speed centrifugation (1000×g, 10 min.). Tenfold dilutions were made in nuclease reaction cocktail buffer (100 mM Tris-HCl, pH 8.8, 10 mM $CaCl_2$, 0.1% NP40) and boiled for 1 minute. 5 μl of each dilution was added to 14 μl of reaction cocktail buffer containing 500 ng of lambda phage DNA (HindIII fragments) and incubated at 37° C. for 2 hours. Reaction products were electrophoresed on 0.8% agarose gels and DNA was visualized by ethidium bromide staining.

EXAMPLE 8

Expression of Vpr1- and Vpx2- SN and SN* fusion proteins in mammalian cells

Figure 2:
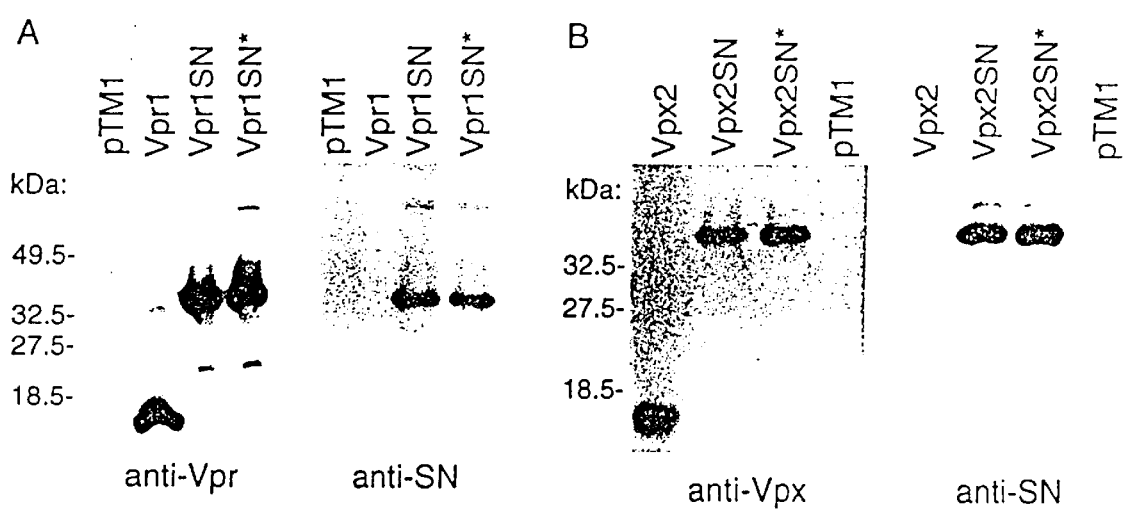
FIGS. 2A and 2B show the expression of Vpr1- and Vpx2- SN and SN* fusion proteins in mammalian cells.

Expression of Vpr1- and Vpx2- SN/SN* fusion proteins in mammalian cells was assessed using the recombinant vaccinia virus-T7 system (rVT7). HeLa cells were grown to 75–80% confluency and transfected with the recombinant plasmids pTM-vpr, pTM-vpx, pTM-vpr1SN/SN*, and pTM-vpx2SN/SN* (FIG. 1). Twenty-four hours after transfection, cells were washed twice with PBS and lysed. Soluble proteins were separated by SDS-PAGE and subjected to immunoblot analysis. The results are shown in FIG. 2. Transfection of pTM-vpr1SN and pTM-vpR1SN* resulted in the expression of a 34 kDa fusion protein that was detectable using both anti-Vpr and anti-SN antibodies (A). Similarly, transfection of pTM-vpx2SN and pTM-vpx2SN* resulted in the expression of a 35 kDa fusion protein which was detected using anti-Vpx and anti-SN antibodies (B). Both fusion proteins were found to migrate slightly slower than expected, based on the combined molecular weights of Vpr1 (14.5 kDa) and SN (16 kDa) and Vpx2 (15 kDa) and SN, respectively. Transfection of pTM-vpr1 and pTM-vpx2 alone yielded appropriately sized wild-type Vpr and Vpx proteins. Anti-Vpr, anti-Vpx and anti-SN antibodies were not reactive with lysates of pTM1 transfected cells included as controls. Thus, both SN and SN* fusion proteins can be expressed in mammalian cells.

EXAMPLE 9

Figure 3:
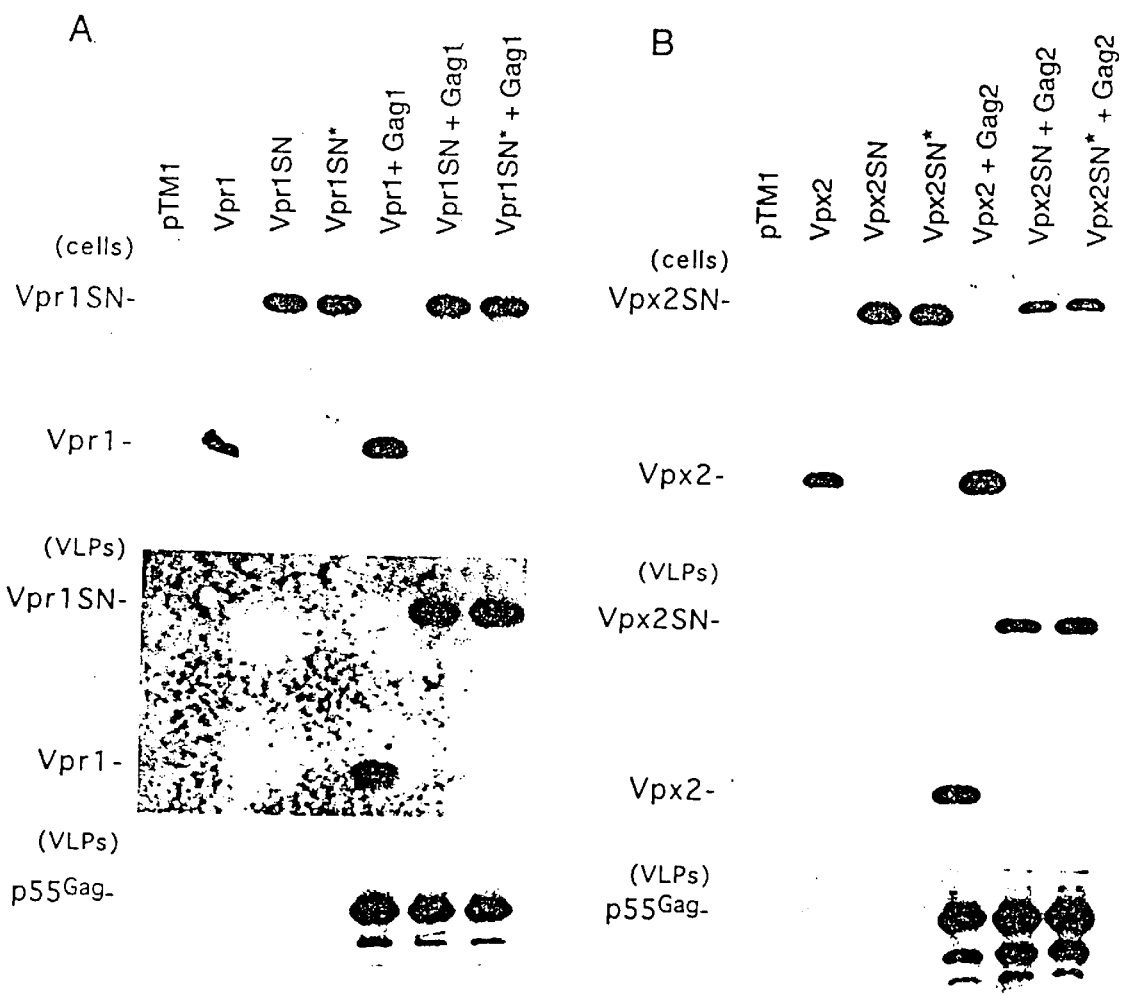
FIGS. 3A and 3B show the incorporation of Vpr1- and Vpx2- SN and SN* fusion proteins into virus-like particles (VLP).

Incorporation of Vpr1- and Vpx2- SN/SN* fusion proteins into virus-like particles In vaccinia and baculovirus systems, the expression of HIV Gag is sufficient for assembly and extracellular release of VLPs. Vpr1 and Vpx2 can be efficiently incorporated into Gag particles without the expression of other viral gene products. To demonstrate that the Vpr1 and Vpx2 fusion proteins could be packaged into VLPs, recombinant plasmids were coexpressed with HIV-1 and HIV-2 Gag proteins in the rVT7 system. pTM-vpr1, pTM-vpr1SN and pTM-vpr1SN* were transfected into HeLa cells alone and in combination with the HIV-1 Gag expression plasmid, pTM-gag1. Twenty-four hours after transfection, cell and VLP extracts were prepared and analyzed by immunoblot analysis (FIG. 3A). Anti-Vpr antibody detected Vpr1, Vpr1SN and Vpr1SN* in cell lysates (top panel) and in pelleted VLPs derived by coexpression with pTM-gag1 (middle panel). In the absence of HIV-1 Gag expression, Vpr1 and Vpr1SN were not detected in pellets of culture supernatants (middle panel). As expected VLPs also contained p55 Gag (bottom panel). Thus, Vpr1SN/SN* fusion proteins were successfully packaged into VLPs.

To demonstrate that Vpx2SN was similarly capable of packaging into HIV-2 VLPs, pTM-vpx2, pTM-vpx2SN and pTM-vpx2SN* were transfected into HeLa cells alone and in combination with the HIV-2 Gag expression plasmid, pTM-gag2. Western blots were prepared with lysates of cells and VLPs concentrated from culture supernatants by ultracentrifugation (FIG. 3B). Anti-Vpx antibody detected Vpx2, Vpx2SN and Vpx2SN* in cell lysates (top panel) and in VLPs derived by coexpression with pTM-gag2 (middle panel). Anti-Gag antibody detected p55 Gag in VLP pellets (bottom panel). Comparison of the relative protein signal intensities suggested that the Vpr1- and Vpx2- SN and SN* fusion proteins were packaged into VLPs in amounts similar to wild-type Vpr1 and Vpx2 proteins. Sucrose gradient analysis of VLPs containing Vpr1SN and Vpx2SN demonstrated co-sedimentation of these fusion proteins with VLPs (data not shown).

Figure 4:
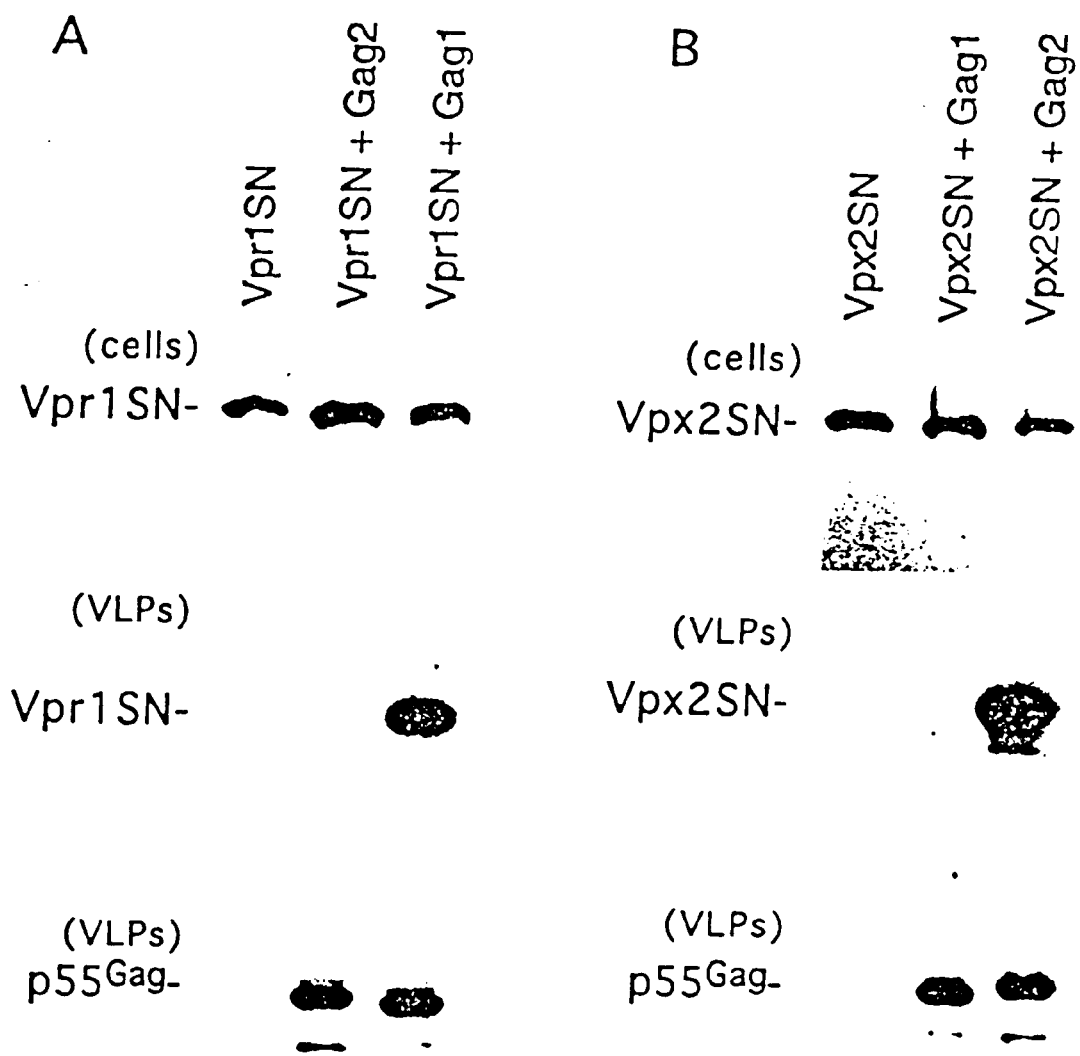
FIGS. 4A and 4B show that virus-specific signals mediate incorporation of Vpr- and Vpx- SN into VLPs.

The Gag C terminal region is required for incorporation of Vpr1 and Vpx2 into virions. However, packaging was found to be virus type-specific, that is, when expressed in trans, Vpx2 was only efficiently incorporated into HIV-2 virions and HIV-2 VLPs. Similarly, HIV-1 Vpr required interaction with the HIV-1 Gag precursor for incorporation into HIV-1 VLPs. To show that the association of Vpr1SN and Vpx2SN with VLPs was not mediated by the SN moiety, but was due to Vpr and Vpx specific packaging signals, pTM-vpr1SN and pTM-vpx2SN were cotransfected individually with either pTM-gag1 or pTM-gag2. For control, pTM-vpr1 and pTM-vpx2 were also transfected alone. Twenty-four hours later, lysates of cells and pelleted VLPs were examined by immunoblotting (FIG. 4). While Vpr1SN was expressed in all cells (FIG. 4A, top panel), and was only associated with VLPs derived from cells transfected with pTM-gag1. Similarly, Vpx2SN was detected in all pTM-vpx2 transfected cells (FIG. 4B, top panel), but was only associated with VLPs derived by cotransfection with pTM-gag2 (FIG. 4B, middle panel). HIV-1 and HIV-2 Gag monoclonal antibodies confirmed the presence of Gag precursor protein in each VLP pellet (FIG. 4B, bottom panels). Thus, incorporation of Vpr1SN and Vpx2SN into VLPs requires interaction of the cognate Gag precursor protein, just like native Vpr1 and Vpx2.

Figure 5:
FIGS. 5A and 5B show a competition analysis of Vpr1SN and Vpx2SN for incorporation into VLPs.
Figure 5:
Figure 5:
Figure 5:

While Vpr1SN and Vpx2SN fusion proteins clearly associated with VLPs (FIG. 3), the question remained whether they would continue to do so in the presence of the native accessory proteins. The efficiency of Vpr1SN and Vpx2SN packaging was compared by competition analysis (FIG. 5). pTM-vpr1SN and pTM-vpx2SN were cotransfected with pTM-gag1/pTM-vpr1 and pTMgag2/pTM-vpx2, respectively, using ratios that ranged from 1:4 to 4:1 (FIG. 5A and FIG. 5B, left panels). For comparison, pTM-vpr1SN and pTM-vpr1 were transfected individually with pTM-gag1 (FIG. 5A, middle and right panels respectively) and pTM-vpx2SN and pTM-vpx2 were transfected with pTM-gag2 (FIG. 5B, middle and right panels respectively). VLPs were pelleted through sucrose cushions, lysed, separated by PAGE, blotted onto nitrocellulose and probed with anti-SN antibody. The results revealed the presence of both Vpr1 and Vpr1SN in VLPs when cotransfected into the same cells (FIG. 5A, left panel). Similarly, coexpressed Vpx2 and Vpx2SN were also copackaged (FIG. 5B, left panel). Comparison of the relative amounts of VLP-associated Vpr1SN and Vpx2SN when expressed in the presence and absence of the native protein, indicated that there were no significant packaging differences. Thus, Vpr1/Vpx2 fusion proteins can efficiently compete with wild-type proteins for virion incorporation.

EXAMPLE 10
Vpr1SN and Vpx2SN fusion proteins possess nuclease activity

Figure 6:
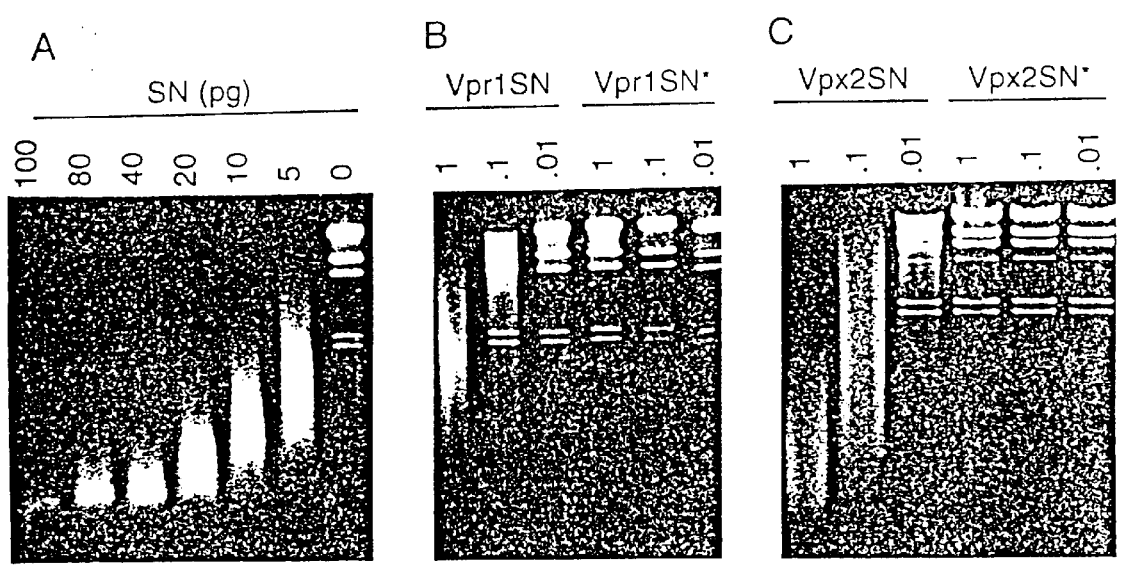
FIGS. 6A–6C show the nuclease activity of VLP-associated Vpr1SN and Vpx2SN proteins. Virus-like particles were concentrated from culture supernatants of T7 expressing HeLa cells cotransfected with pTM-gag1/pTM-vpr1SN, pTM-gag1/pTM-vpr1SN*, pTM-gag2/pTM-vpx2SN and pTM-gag2/pTM-vpx2SN* by ultracentrifugation (125,000×g, 2 hrs.) through 20% cushions of sucrose. Pellets containing Vpr1- SN and SN* (B) and Vpx2- SN and SN* (C) were resuspended in PBS. Tenfold dilutions were made in nuclease reaction cocktail buffer (100 mM Tris-HCl pH 8.8, 10 mM $CaCl_2$, 0.1% NP40) and boiled for 1 minute. 5 ul of each dilution was added to 14 ul of reaction cocktail buffer containing 500 ng of lambda phage DNA (HindIII fragments) and incubated at 37° C. for 2 hours. Reaction products were electrophoresed on 0.8% agarose gels and DNA was visualized by ethidium bromide staining. Standards (A) were prepared by dilution of purified staphylococcal nuclease (provided by A. Mildvan) into cocktail buffer and assayed.

To demonstrate that virion associated SN fusion proteins were enzymatically active, VLPs concentrated by ultracentrifugation from culture supernatants of HeLa cells transfected with pTM-gag1/pTM-vpr1SN and pTM-gag2/pTM-vpx2SN were analyzed for nuclease activity using an in vitro DNA digestion assay. Prior to this analysis, immunoblotting confirmed the association of Vpr1SN and Vpx2SN with VLPs (data not shown). FIG. 6 shows lambda phage DNA fragments in 0.8% agarose gels after incubation with dilutions of VLPs lysates that contained Vpr1- or Vpx2- SN fusion proteins. VLPs containing Vpr1SN* and Vpx2SN* were included as negative controls and dilutions of purified SN served as reference standards (FIG. 6A). Both virion associated Vpr1SN (FIG. 6B) and Vpx2SN (FIG. 6C) fusion proteins exhibited nuclease activity as demonstrated by degradation of lambda phage DNA. Cell-associated Vpr1SN and Vpx2SN fusion proteins also possessed nuclease activity when analyzed in this system (data not shown). To control for SN specificity, this analysis was also conducted in buffers devoid of $Ca^{++}$ and under these conditions no SN activity was detected (data not shown). Thus, SN remains enzymatically active when expressed as a fusion protein and packaged into VLPs.

EXAMPLE 11
Incorporation of Vpx2SN fusion protein into HIV-2 virions

Vpx is incorporated into HIV-2 virions when expressed in trans. To show that Vpx2 fusion proteins were similarly capable of packaging into wild-type HIV-2 virions, an expression plasmid (pLR2P) was constructed placing the vpx2SN and vpx2SN* coding regions under control of HIV-2 LTR and RRE elements. The HIV-2 RRE was positioned downstream of the fusion genes to ensure mRNA stability and efficient translation (FIG. 7A). To show that the fusion proteins could package when expressed in trans, HIV-$2_{ST}$ proviral DNA (pSXB1) was transfected alone and in combination with pLR2P-vpx2SN and pLR2P-vpx2SN*. Forty-eight hours later, extracellular virus was pelleted from culture supernatants by ultracentrifugation through cushions of 20% sucrose and examined by immunoblot analysis (FIG. 7B). Duplicate blots were probed using anti-Vpx (left), anti-SN (middle) and anti-Gag (right) antibodies. Anti-Vpx antibody detected the 15 kDa Vpx2 protein in all viral pellets. In virions derived by cotransfection of HIV-2ST with pLR2P-vpx2SN and pLR2P-vpx2SN*, additional proteins of approximately 35 and 32 kDa were clearly visible. The same two proteins were also apparent on a duplicate blot probed with anti-SN antibodies, indicating that they represented Vpx2SN fusion proteins (FIG. 7B, middle panel). The predicted molecular weight of full-length Vpx2SN fusion protein is 33 kDa. As native Vpx and SN run slightly slower than predicted, it is likely that the 35 kDa species represents the full-length Vpx2SN fusion protein. Anti-SN antibodies detected additional proteins of approximately 21 and 17 kDa (these proteins were more apparent after longer exposure). Since only the 35 kDa protein was detected in Gag derived VLPs, which lack Pol proteins (FIG. 2), the smaller proteins represented cleavage products of Vpx2SN and Vpx2SN* generated by the viral protease. Anti-Gag antibodies confirmed the analysis of approximately equivalent amounts of virions from each transfection.

To show packaging of Vpx2SN into HIV-2 virions, sucrose gradient analysis was performed. Extracellular virus collected from culture supernatants of HLtat cells forty-eight hours after cotransfection with pLR2P-vpx2SN and HIV-2ST was pelleted through cushions of 20% sucrose. Pellets were resuspended in PBS and then centrifuged for 18 hours over linear gradients of 20–60% sucrose. Fractions were collected and analyzed by immunoblotting (FIG. 7C). Duplicate blots were probed separately with anti-SN (top) and anti-Gag (bottom) antibodies. Peak concentrations of both Vpx2SN and Gag were detected in fractions 8–11, demonstrating direct association and packaging of Vpx2SN into HIV-2 virions. These same sucrose fractions (8–11) were found to have densities between 1.16 and 1.17 g/ml, as determined by refractometric analysis (data not shown). Again, both the 35 kDa and 32 kDa forms of Vpx2SN were detected, providing further evidence for protease cleavage following packaging into virus particles.

Since HIV-2ST is defective in vpr, this may have affected the packaging of the Vpx2SN fusion protein. A second strain of HIV-2, termed HIV-$2_{731}$ 2A, was analyzed which was cloned from short-term PBMC culture and contains open reading frames for all genes, including intact vpr and vpx genes (unpublished). A plasmid clone of HIV-$2_{7312A}$ proviral DNA (pJK) was transfected alone and in combination with pLR2P-vpx2SN into HLtat cells. For comparison, HIV-$2_{ST}$ was also co-transfected with pLR2P-vpx2SN. Progeny virus was concentrated by ultracentrifugation through sucrose cushions and examined by immunoblot analysis (FIG. 7D). Duplicate blots were probed with anti-Vpx (left) and anti-Gag (right) antibodies. The results revealed comparable levels of Vpx2SN incorporation into vpr competent virus (HIV-$2_{7312A}$) compared with vpr-defective virus (HIV-$2_{ST}$). Moreover, the 35 kDa and 32 kDa proteins were again detected in HIV-$2_{7312A}$ virions. Thus, efficient incorporation of the Vpx2SN protein into replication-competent wild-type HIV-2 was demonstrated, even in the presence of native Vpr and Vpx proteins.

EXAMPLE 12
Incorporation of Vpr1SN into HIV-1 virions

Figure 8:
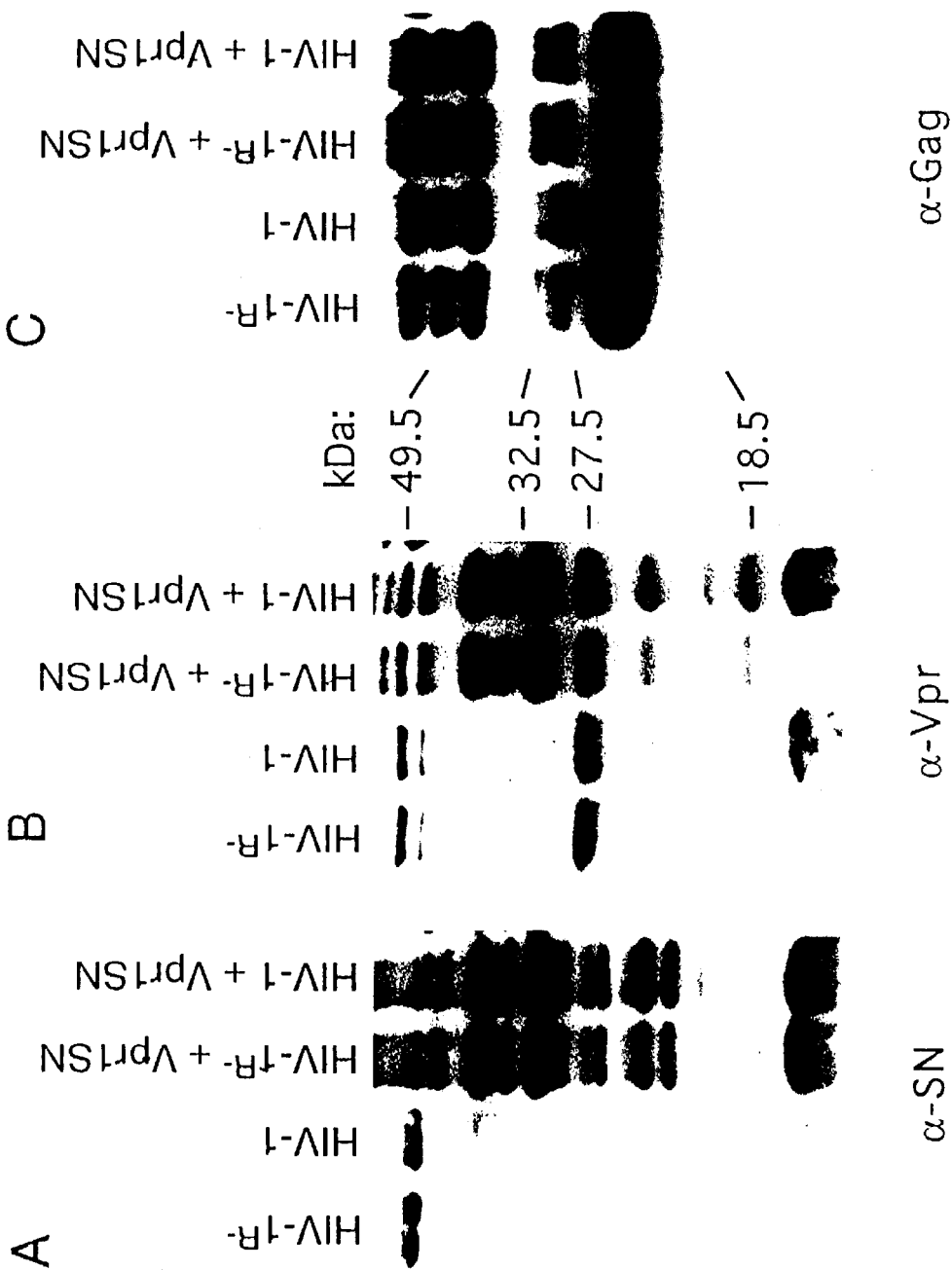
FIGS. 8A–8C show the incorporation of Vpr1SN into HIV-1 virions by trans complementation. Culture supernatant virus from HLtat cells transfected with pNL4-3 (HIV-1) and pNL4-3R⁻ (HIV-1 vpr mutant) or cotransfected with pNL4-3/pLR2P-vpr1SN and pNL4-3R⁻/pLR2P-vpr1SN was presence of an HIV protease inhibitor, they must represent cleavage products produced by the viral protease. Taken together, these results demonstrate that Vpr and Vpx can be used to target functional proteins, including potentially deleterious enzymes, to the HIV/SIV particle. These properties are useful for the development of novel antiviral strategies.

Using the same LTR/RRE-based expression plasmid, it was also shown that Vpr1SN could package into HIV-1 virions by coexpression with HIV-1 provirus (as discussed above, the HIV-2 LTR can be transactivated by HIV-1 Tat and the HIV-2 RRE is sensitive to the HIV-1 Rev protein). Virions released into the culture medium 48 hours after transfection of HLtat cells with pNL4-3 (HIV-1) and pNL4-3-R⁻ (HIV-1-R⁻) alone and in combination with pLR2P-vpr1SN were concentrated by ultracentrifugation and examined by immunoblot analysis (FIG. 8). As observed in cotransfection experiments with HIV-2, anti-SN antibodies identified two major Vpr1SN fusion proteins of approximately 34 and 31 kDa. These proteins were not detected in virions produced by transfection of pNL4-3 and pNL4-3-R⁻ alone. From expression in the rVT7 system, the full-length Vpr1SN fusion protein was expected to migrate at 34 kDa. Therefore, the 31 kDa protein likely represents a cleavage product. Anti-SN antibodies also detected a protein migrating at 17 kDa. Anti-Vpr antibody detected the 34 and 31 kDa proteins in virions derived from cotransfected cells. It is noteworthy that both the anti-Vpr and anti-SN antibodies detected the 31 kDa protein most strongly, and that anti-Vpr antibody did not detect the 17 kDA protein recognized by anti-SN antibody. These results also show that even in virions in which native Vpr protein was packaged, Vpr1SN was also incorporated in abundance. Gag monoclonal antibody detected similar amounts of Gag protein in all viral pellets and demonstrated processing of the p55$^{Gag}$ precursor (FIG. 8C).

To demonstrate more directly that cleavage of the Vpr1- and Vpx2-SN fusion proteins was mediated by the HIV protease, virus was concentrated from pNL4-3-R⁻/pLR2P-vpr1SN and pSXB1/pLR2P-vpx2SN transfected cells that were cultured in the presence of 1 μM of the HIV protease inhibitor L-689,502 (provided by Dr. E. Emini, Merck & Co. Inc.). As expected, immunoblot analysis of virions demonstrated substantially less processing of p55$^{Gag}$ (FIG. 9A). Similarly, virions produced in the presence of L-689,502 also contained greater amounts of the uncleaved species of Vpr1SN and Vpx2SN fusion proteins (FIG. 9B). Taken together, these results demonstrate that Vpr1- and Vpx2- SN fusion proteins are subject to protease cleavage during or subsequent to virus assembly.

Figure 10:
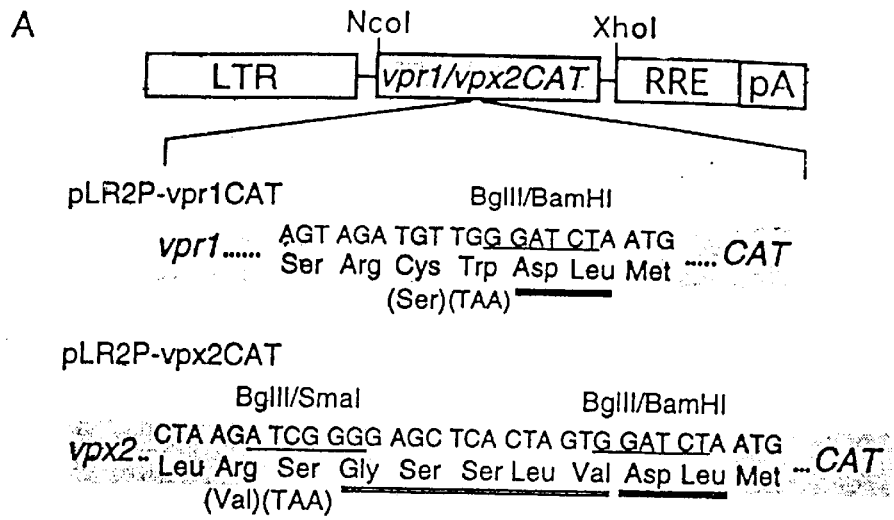
Figure 10:
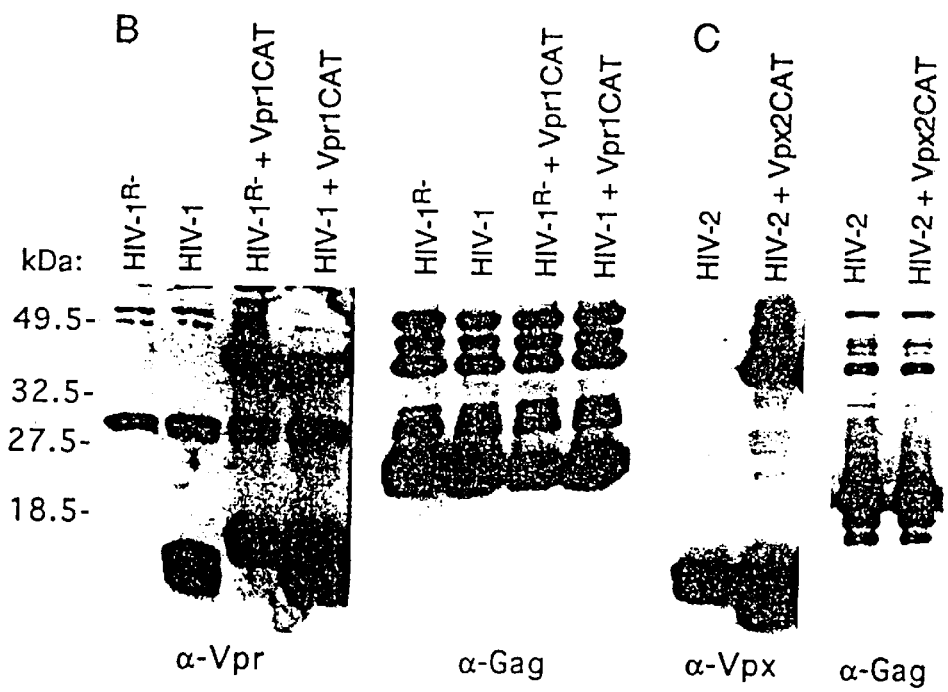
Figure 10:
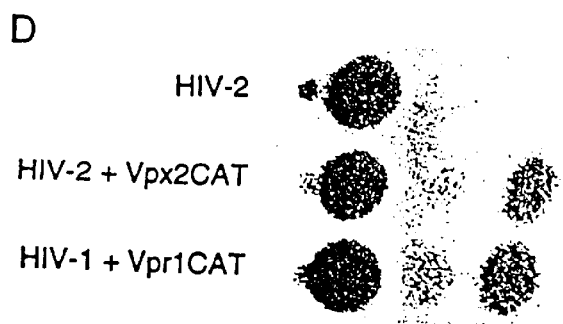

EXAMPLE 13
Vpr1-CAT and Vpx2-CAT fusion protein incorporation into HIV virions To show that Vpx2 and Vpr1 could target additional proteins to the HIV particle, the entire 740 bp CAT gene was substituted for SN in the pLR2P-vpx2SN and pLR2P-vpr1SN vectors, generating pLR2P-vpr1CAT and pLR2P-vpx2CAT (FIG. 10A). pNL4-3/pLR2P-vpr1CAT, pNL4-3-R⁻/pLR2P-vpr1CAT and pSXB1/pLR2P-vpx2CAT were co-transfected into HLtat cells. As controls, pNL4-3, pNL4-3-R⁻ and pSXB1 were transfected alone. Progeny virions, concentrated from culture supernatants, were analyzed by immunoblotting (FIGS. 10B and 10C). Using anti-Vpr antibodies, 40 kDa fusion proteins were detected in viral pellets derived by co-transfection of pRL2P-vpr1CAT with both pNL4-3 and pNL4-3-R⁻ (FIG. 10B). This size is consistent with the predicted molecular weight of the full-length Vpr1CAT fusion protein. In addition, anti-Vpr antibodies also detected a 17 kDa protein which did not correspond to the molecular weight of native Vpr1 protein (14.5 kDa in virions derived from cells transfected with pNL4-3). The same protein was recognized weakly with anti-CAT antibodies, suggesting a fusion protein cleavage product containing mostly Vpr sequence. Very similar results were obtained with virions derived from HLtat cells co-transfected with HIV-2ST and pRL2P-vpx2CAT, in which anti-Vpx antibody detected 41 and 15 kDa proteins (FIG. 10C). These results demonstrate that Vpr1CAT and Vpx2CAT fusion proteins are packaged into virions. However, like in the case of SN fusion proteins, CAT fusion proteins were also cleaved by the HIV protease (the Vpx2CAT cleavage product is not visible because of co-migration with the native Vpx protein. CAT cleavage appeared less extensive, based on the intensity of the full-length CAT fusion protein on immunoblots.

Lysates of HIV-1 and HIV-2 viral particles were diluted 1:50 in 20 mM Tris-base and analyzed for CAT activity by the method of Allon, et al., Nature 282:864–869 (1979). FIG. 10D indicates that virions which contained Vpr1CAT and Vpx2CAT proteins possessed CAT activity. These results show the packaging of active Vpr1- and Vpx2- CAT fusion proteins.

Figure 11:

EXAMPLE 14
Virion incorporated SN and CAT fusion proteins are enzymatically active The ability of Vpr1 and Vpx2 to deliver functionally active proteins to the virus particle was further confirmed by sucrose gradient analysis. Virions derived from HLtat cells co-transfected with HIV-2$_{ST}$ and pLR2P-vpx2 were sedimented in linear gradients of 20–60% sucrose as described above. Fractions were collected and analyzed for viral Gag protein (FIG. 11 A) and corresponding CAT activity (FIG. 11B). Peak amounts of Gag protein were detected in fractions 6 and 7 (density 1.16 and 1.17, respectively). Similarly, peak amounts of acetylated chloramphenicol (Ac-cm) were also detected in fractions 6 and 7.

Whether virion associated SN fusion protein retained nuclease activity was also shown. HIV-1$_{SG3}$ virions containing Vpr1SN were analyzed after sedimentation in linear gradients of sucrose (FIG. 11). Since the present invention demonstrated that protease cleavage of SN fusion proteins (FIGS. 7, 8 and 9) markedly reduced Vpr1SN nuclease activity (data not shown), these experiments were performed by culturing pSG3/pLR2P-vpr1SN co-transfected cells in the presence of L-689,502 as described above. Immunoblot analysis of sedimented virions revealed peak concentrations of Gag in fractions 6 and 7 and substantially reduced p55 processing (FIG. 11C). Peak SN activity was associated with the fractions that contained the highest concentrations of virus (FIG. 11D). These results thus document that virion incorporation per se does not abrogate the enzymatic activity of Vpr/Vpx fusion proteins, although cleavage by the viral protease may inactivate the fusion partners.

The present invention demonstrated the capability of HIV-1 Vpr and HIV-2 Vpx to direct the packaging of foreign proteins into HIV virions when expressed as heterologous fusion molecules. The trans complementation experiments with HIV proviral DNA revealed that Vpr1 and Vpx2 fusion proteins were also incorporated into replication-competent viruses. Moreover, packaging of the fusion proteins in the presence of wild-type Vpx and/or Vpr proteins (FIGS. 5, 7 and 8) indicated that the viral signals mediating their packaging were not obstructed by the foreign components of the fusion molecules. Likewise, virion-associated SN and CAT fusion proteins remained enzymatically active.

Based on the immunoblot analysis of VLPs and virions, the present invention illustrates that both virion associated CAT and SN/SN* are susceptible to cleavage by the viral protease. There appears to be at least one cleavage site in CAT and two cleavage sites in the SN/SN* proteins. Based on calculated molecular weights of the major SN/SN* cleavage products, it appears that SN and SN* are cleaved once near their C termini and once near the fusion protein junctions. Since the fusion protein junctions of Vpr1SN and Vpx2SN are not identical it is also possible that these regions differ with respect to their susceptibility to the viral protease. Although Vpx2SN/SN* were processed to a lesser extent than Vpr1SN (FIGS. 7 and 8), the major cleavage sites appear to be conserved. There is no doubt that both the HIV-1 and HIV-2 proteases recognize processing sites in the fusion partners and that there is sufficient physical contact to enable cleavage. This is evidenced both by the reduction of cleavage product intensities on immunoblots as well as by an increased enzymatic activity in the presence of an HIV protease inhibitor.

The demonstration that Vpr1 and Vpx2 fusion proteins are capable of associating with both VLPs and virions facilitates studies on these accessory proteins and on HIV assembly in general. The approach of generating deletion mutants to study protein structure/function relationships is often of limited value since this can reduce protein stability or change the three dimensional structure of the protein. In the case of Vpr, a single amino acid substitution at residue 76 has been shown to destabilize its expression in infected cells. Studies have indicated that deletion mutations in vpr and vpx result in premature degradation of the proteins following expression. Fusion of Vpr and Vpx mutant proteins with, e.g., SN or CAT as demonstrated by the present invention, increase stability.

The successful packaging of Vpr1/Vpx2SN fusion proteins into virions indicates their use for accessory protein targeted viral inactivation. The present invention demonstrates that Vpr and Vpx may serve as vehicles for specific targeting of virus inhibitory molecules, including SN. In contrast to HIV Gag, Vpr and Vpx are small proteins that can be manipulated relatively easily without altering virus replication and thus may represent vehicles with considerable versatility for application to such an antiviral strategy.

The present invention demonstrated that Vpr and Vpx can serve as vehicles to deliver functionally active enzymes to the HIV virion, including those that may exert an antiviral activity such as SN. The present invention has demonstrated that the concept of accessory protein targeted virus inactivation is feasible.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A DNA segment for inhibiting replication of a virus in trans comprising:
  a Vpr gene that expresses a Vpr polypeptide, said Vpr polypeptide serving in replication of said virus; and
  a virus inhibitory protein gene fused to said Vpr gene wherein said virus inhibitory protein gene encodes for a polypeptide selected from a group consisting of: protease, integrase, reverse transcriptase, Vif, Nef and Gag.

2. A DNA segment comprising:
  a Vpr gene fragment that expresses a Vpr polypeptide; and
  a second gene fragment differing from said Vpr gene fragment, said second fragment coupled to said Vpr gene fragment wherein said second gene fragment encodes for a polypeptide independent of staphylococcal nuclease and the DNA segment is expressed in trans genomic Gag.

3. The DNA segment of claim 2 wherein said segment is incorporated into a virion.

4. A DNA segment for inhibiting replication of a virus in trans comprising:
  a Vpx gene that expresses a Vpx polypeptide, said Vpx polypeptide lacking an inhibitory effect on said virus serving in replication of said virus; and
  a virus inhibitory protein gene fused to said Vpx gene.

5. A DNA segment comprising:
  a Vpx gene fragment that expresses a Vpx polypeptide and lacks an inhibitory effect on said virus; and
  a second gene fragment differing from said Vpx gene fragment, said second fragment coupled to said Vpx gene fragment, wherein said second fragment encodes for a polypeptide independent of staphylococcal nuclease and the DNA segment is expressed in trans to genomic Gag.

6. The DNA segment of claim 5 wherein said segment is incorporated into a virion.

7. A vector for inhibiting replication of a virus in trans comprising:
  a first nucleic acid sequence of a sufficient length to encode for a protein active in replication of said retrovirus, said first nucleic acid sequence lacking an inhibitory effect on said virions;
  a second nucleic acid sequence fused to said first nucleic acid sequence, said second nucleic acid sequence of sufficient length to encode for a virus inhibitory protein such that expression of both said first and said second nucleic acid sequence occurs upon expression of either nucleic acid sequence; and
  a control element operatively-linked to said first nucleic acid sequence and directing synthesis of said protein active in viral replication.

8. The vector of claim 7 wherein said control element is HIV-2 RRE.

9. The vector of claim 7 wherein said control element is HIV-2 LTR.

10. A cell line transformed with the vector of claim 7.

11. A vector for inhibiting replication of a virus in trans comprising:
  a first nucleic acid sequence of a sufficient length to encode for a protein active in replication of said virus and lacking an inhibitory effect on said virus, wherein said protein functions in nuclear transport of a viral pre-integration complex;
  a second nucleic acid sequence fused to said first nucleic acid sequence, said second nucleic acid sequence of sufficient length to encode for a virus inhibitory protein such that expression of both said first and said second nucleic acid sequence occurs upon expression of either nucleic acid sequence and virus inhibitory protein is selected from a group consisting of protease, integrase, reverse transcriptase, Vif Nef and Gag; and
  a control element operatively-linked to said first nucleic acid sequence and directing synthesis of said protein active in viral replication.

12. A vector comprising:
  a first nucleic acid sequence of sufficient length to encode for a first polypeptide, said first polypeptide being active in replication of a virion and lacking an inhibitory effect on said virus;
  a second nucleic acid sequence fused to said first nucleic acid sequence, said second nucleic acid sequence of sufficient length to encode for a second polypeptide such that expression of both said first and said second nucleic acid sequence in trans to genomic Gag occurs upon expression of either nucleic acid sequence; and
  a control element operatively-linked to said first and said second nucleic acid sequences and directing synthesis of said first polypeptide.

13. The vector of claim 12 wherein said first polypeptide is active in HIV-1 replication.

14. The vector of claim 12 wherein said control elements further comprise additional regulatory elements.

15. The vector of claim 14 wherein said additional regulatory elements comprise components selected from a group consisting of: HIV2-LTR and HIV2-RRE.

16. The vector of claim 12 wherein said first nucleic acid sequence and said second nucleic acid sequence are both DNA.

17. The vector of claim 12 wherein said first nucleic acid sequence and said second nucleic acid sequence are both RNA.

18. The vector of claim 12 wherein said first and second nucleic acid sequence is incorporated into a virion.

19. The vector of claim 12 wherein said second polypeptide is heterologous to said virion.

20. The vector of claim 12 wherein said second polypeptide is homologous to said virion.

21. The vector of claim 12 wherein said second polypeptide is expressed in a host wherein said host is selected from a group consisting of: bacterial cells, mammalian cells and insect cells.

22. A vector comprising:

a first nucleic acid sequence of sufficient length to encode of a first polypeptide, wherein said first polypeptide functions in nuclear transport;

a second nucleic acid sequence fused to said first nucleic acid sequence said second nucleic acid sequence of sufficient length to encode for a second polypeptide such that expression of both first and said second nucleic acid sequence in tans to genomic Gag occurs upon expression of either nucleic acid sequence and said second polypeptide is selected from a group consisting of chloramphericol acetyl transferase, protease, integrase, reverse transcriptase, Vif, Nef and Gag; and a control element operative-linked to said first and said second nucleic acid sequences and directing synthesis of said first polypeptide.

23. A vector comprising:

a first nucleic acid sequence of sufficient length to encode a first polypeptide, wherein said first polypeptide is a Vpr fragment;

a second nucleic acid sequence fused to said first nucleic acid sequence said second nucleic acid sequence of sufficient length to encode for a second polypeptide such that expression of both said first and said second nucleic acid sequence occurs upon expression in trans to genomic Gag of either nucleic acid sequence and said second polypeptide is selected from a group consisting of chloramphericol acetyl transferase, protease, integrase, reverse transcriptase, Vif, Nef and Gag; and a control element operative-linked to said first and said second nucleic acid sequences and directing synthesis of said first polypeptide.

24. A vector comprising:

a first nucleic acid sequence of sufficient length to encode a first polypeptide, wherein said first polypeptide is a Vpx fragment;

a second nucleic acid sequence fused to said first nucleic acid sequence said second nucleic acid sequence of sufficient length to encode for a second polypeptide such that expression of both said first and said second nucleic acid sequence occurs upon expression in trans to genomic Gag of either nucleic acid sequence and said second polypeptide is selected from a group consisting of chloramphericol acetyl transferase, protease, integrase, reverse transcriptase, Vif, Nef and Gag; and control elements operative-linked to said first and said second nucleic acid sequences and directing synthesis of said first polypeptide.

* * * * *

UNITED STATES PATENT AND TRADEMARK OFFICE
CERTIFICATE OF CORRECTION

PATENT NO. : 6,001,985
APPLICATION NO. : 08/947516
DATED : December 14, 1999
INVENTOR(S) : Kappes and Wu Page 1 of 1

It is certified that error appears in the above-identified patent and that said Letters Patent is hereby corrected as shown below:

In the Specification

Please insert the following paragraph directly under the Description section and before the Background of the Invention section:
--GOVERNMENT SUPPORT CLAUSE
This invention was made with government support under grant numbers AI031816 and CA073470 awarded by the National Institutes of Health. The government has certain rights in the invention.--

Signed and Sealed this
Twenty-ninth Day of December, 2020

Andrei Iancu
*Director of the United States Patent and Trademark Office*